US012805833B2

(12) United States Patent
Naik et al.

(10) Patent No.: US 12,805,833 B2
(45) Date of Patent: Nov. 24, 2026

(54) HYBRID TIME DOMAIN MULTIPLEXING AND FREQUENCY DOMAIN MULTIPLEXING CONFIGURATIONS FOR ULTRASOUND FETAL HEART RATE MONITORING SYSTEMS

(71) Applicant: GE Precision Healthcare LLC, Waukesha, WI (US)

(72) Inventors: Rajendra Naik, Bangalore (IN); Shrihari Viswanath, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 306 days.

(21) Appl. No.: 18/426,544

(22) Filed: Jan. 30, 2024

(65) Prior Publication Data

US 2025/0241615 A1 Jul. 31, 2025

(51) Int. Cl.

*A61B 8/08* (2006.01)
*A61B 8/00* (2006.01)
*A61B 8/02* (2006.01)

(52) U.S. Cl.

CPC .............. *A61B 8/0866* (2013.01); *A61B 8/02* (2013.01); *A61B 8/488* (2013.01); *A61B 8/56* (2013.01)

(58) Field of Classification Search

CPC ..... A61B 8/0866; A61B 8/488; A61B 8/4477; A61B 8/02

See application file for complete search history.

(56) References Cited

U.S. PATENT DOCUMENTS 5,088,497 A 2/1992 Ikeda
5,528,168 A 6/1996 Kleveland
(Continued)

FOREIGN PATENT DOCUMENTS

CN 105342640 B 2/2016
CN 105913355 A 8/2016
(Continued)

OTHER PUBLICATIONS

Non-Final Office Action received for U.S. Appl. No. 18/426,572 dated May 5, 2025, 9 pages.
(Continued)

*Primary Examiner* — Anhtuan T Nguyen
*Assistant Examiner* — Younhee Choi
(74) *Attorney, Agent, or Firm* — Amin, Turocy & Watson, LLP

(57) ABSTRACT

A hybrid time domain multiplexing (TDM) and frequency domain multiplexing (FDM) configuration protocol for a doppler-based ultrasound fetal monitoring system (FMS) is provided. In an example, an FMS determines context information regarding an operating context of the FMS, the context information comprising a number of fetal sensor devices (FSDs) activated for monitoring a corresponding number of fetuses of a single mother, wherein each of the FSDs comprise an ultrasound transducer configured to measure fetal parameters of a single fetus, and wherein each of the FSDs is configurable to operate using either the FDM mode or the TDM mode. The FMS further configures respective operating modes (i.e., FDM mode or TDM mode) of the FSDs based on the context information and in accordance with a configuration protocol that varies the respective operating modes (i.e., FDM mode or TDM mode) of the FSDs under different operating contexts of the FMS.

20 Claims, 11 Drawing Sheets

(56) References Cited

U.S. PATENT DOCUMENTS

| | | | |
|---|---|---|---|
| 6,288,577 B1 | 9/2001 | Wong | |
| 6,320,406 B1 | 11/2001 | Morgan et al. | |
| 6,650,149 B1 | 11/2003 | Wong | |
| 6,862,432 B1 | 3/2005 | Kim | |
| 6,963,249 B2 | 11/2005 | Devries et al. | |
| 7,292,119 B2 | 11/2007 | Urakawa | |
| 7,949,444 B2 | 5/2011 | Mukherjee | |
| 7,983,626 B2 | 7/2011 | Kim | |
| 8,055,887 B2 | 11/2011 | Karstens | |
| 8,407,158 B2 | 3/2013 | Suri et al. | |
| 8,696,578 B2 | 4/2014 | Kabakov et al. | |
| 8,738,663 B2 | 5/2014 | Gonzalez et al. | |
| 8,746,548 B2 | 6/2014 | Terwilliger et al. | |
| 9,183,603 B2 | 11/2015 | Borges et al. | |
| 9,396,037 B2 | 7/2016 | Morsi et al. | |
| 9,536,044 B2 | 1/2017 | White et al. | |
| 9,672,458 B2 | 6/2017 | Burkhart et al. | |
| 9,734,448 B2 | 8/2017 | Bolich et al. | |
| 10,025,791 B2 | 7/2018 | Lee | |
| 10,402,781 B2 | 9/2019 | Terwilliger et al. | |
| 10,638,999 B2 | 5/2020 | Shah | |
| 10,789,264 B2 | 9/2020 | Crabtree et al. | |
| 10,810,390 B2 | 10/2020 | Hegendoerfer et al. | |
| 10,901,834 B2 | 1/2021 | Abhinav et al. | |
| 10,902,232 B2 | 1/2021 | Peng | |
| 10,949,440 B2 | 3/2021 | Schoueri et al. | |
| 11,087,878 B2 | 8/2021 | Vesto et al. | |
| 11,240,181 B1 | 2/2022 | Nagaraja et al. | |
| 11,309,060 B2 | 4/2022 | Janevski et al. | |
| 11,321,338 B2 | 5/2022 | Okorafor et al. | |
| 11,327,989 B2 | 5/2022 | Wu et al. | |
| 11,451,201 B1 | 9/2022 | Hoffman et al. | |
| 11,481,738 B2 | 10/2022 | Tong et al. | |
| 11,599,729 B2 | 3/2023 | Wu | |
| 11,842,188 B2 | 12/2023 | Bregman et al. | |
| 2004/0036538 A1 | 2/2004 | Devries et al. | |
| 2004/0090265 A1 | 5/2004 | Pradhan | |
| 2005/0130699 A1 | 6/2005 | Kim | |
| 2005/0134491 A1 | 6/2005 | Huang et al. | |
| 2005/0219003 A1 | 10/2005 | Urakawa | |
| 2006/0241482 A1 | 10/2006 | Karasawa | |
| 2007/0243834 A1 | 10/2007 | Takei | |
| 2007/0260155 A1 | 11/2007 | Rapoport et al. | |
| 2008/0114249 A1* | 5/2008 | Randall | G01S 15/8977 600/447 |
| 2009/0043203 A1 | 2/2009 | Pelissier et al. | |
| 2010/0168596 A1 | 7/2010 | Jaeschke et al. | |
| 2010/0191117 A1 | 7/2010 | Kabakov | |
| 2010/0274145 A1 | 10/2010 | Tupin, Jr. et al. | |
| 2010/0274750 A1 | 10/2010 | Oltean et al. | |
| 2011/0160591 A1* | 6/2011 | Smith | A61B 8/02 600/453 |
| 2011/0254567 A1 | 10/2011 | Gehrig et al. | |
| 2011/0295102 A1 | 12/2011 | Lakkis et al. | |
| 2012/0053465 A1 | 3/2012 | Kudoh | |
| 2012/0123267 A1 | 5/2012 | Dow et al. | |
| 2012/0123302 A1 | 5/2012 | Liu et al. | |
| 2012/0232398 A1 | 9/2012 | Roham et al. | |
| 2012/0286889 A1 | 11/2012 | Park et al. | |
| 2013/0087609 A1 | 4/2013 | Nichol et al. | |
| 2013/0123637 A1 | 5/2013 | Wohlschlager et al. | |
| 2013/0158407 A1 | 6/2013 | Kabakov et al. | |
| 2013/0245436 A1 | 9/2013 | Tupin, Jr. et al. | |
| 2014/0163378 A1 | 6/2014 | Ohshima | |
| 2014/0276070 A1 | 9/2014 | Kabakov et al. | |
| 2015/0146772 A1 | 5/2015 | Fujimori | |
| 2015/0219580 A1 | 8/2015 | Gehrig et al. | |
| 2015/0302176 A1 | 10/2015 | Lyons et al. | |
| 2015/0372664 A1 | 12/2015 | Walker et al. | |
| 2016/0204765 A1 | 7/2016 | Ferriss et al. | |
| 2017/0043189 A1 | 2/2017 | Stoddard et al. | |
| 2017/0071579 A1 | 3/2017 | Ko et al. | |
| 2017/0303899 A1 | 10/2017 | Willsie | |
| 2018/0115197 A1 | 4/2018 | Li et al. | |
| 2018/0317878 A1* | 11/2018 | Wohlschlager | A61B 8/02 |
| 2018/0338746 A1 | 11/2018 | Wu et al. | |
| 2019/0019090 A1 | 1/2019 | Chacko et al. | |
| 2019/0370671 A1 | 12/2019 | Canedo et al. | |
| 2020/0261059 A1* | 8/2020 | Xu | A61B 8/06 |
| 2020/0365262 A1 | 11/2020 | Sreenivasan et al. | |
| 2020/0380076 A1 | 12/2020 | Taylor | |
| 2021/0064932 A1 | 3/2021 | Wang et al. | |
| 2021/0241897 A1 | 8/2021 | Casse et al. | |
| 2022/0005083 A1 | 1/2022 | Patterson et al. | |
| 2022/0189618 A1 | 6/2022 | Klassen et al. | |
| 2022/0192525 A1* | 6/2022 | Franck | A61B 8/488 |
| 2022/0233174 A1 | 7/2022 | Hwang | |
| 2022/0265157 A1* | 8/2022 | Charthad | A61B 8/488 |
| 2022/0293246 A1 | 9/2022 | Tweedie et al. | |
| 2022/0337189 A1 | 10/2022 | Huang et al. | |
| 2022/0374300 A1 | 11/2022 | Che et al. | |
| 2023/0034748 A1 | 2/2023 | Bull et al. | |
| 2023/0168895 A1 | 6/2023 | Shah et al. | |
| 2023/0238103 A1 | 7/2023 | Murphy et al. | |
| 2023/0259821 A1 | 8/2023 | Travalini et al. | |
| 2023/0335236 A1 | 10/2023 | Dambman et al. | |
| 2023/0335238 A1 | 10/2023 | Danckwardt | |
| 2023/0338000 A1 | 10/2023 | B et al. | |
| 2024/0296352 A1 | 9/2024 | Yanosy, Jr. et al. | |
| 2025/0241615 A1 | 7/2025 | Naik et al. | |

FOREIGN PATENT DOCUMENTS

| | | | |
|---|---|---|---|
| CN | 108231145 | A | 6/2018 |
| CN | 110035303 | A | 7/2019 |
| CN | 111899852 | A | 11/2020 |
| CN | 112364148 | A | 2/2021 |
| CN | 114073546 | A | 2/2022 |
| CN | 114118062 | A | 3/2022 |
| CN | 114882979 | A | 8/2022 |
| CN | 114898848 | A | 8/2022 |
| CN | 115098673 | A | 9/2022 |
| CN | 115964460 | A | 4/2023 |
| CN | 114446423 | A | 6/2023 |
| EP | 4 278 980 | A1 | 11/2023 |
| WO | 2020/167316 | A1 | 8/2020 |
| WO | 2022206822 | A1 | 10/2022 |
| WO | 2022/229088 | A1 | 11/2022 |
| WO | 2023/088983 | A1 | 5/2023 |

OTHER PUBLICATIONS

Non-Final office action received for U.S. Appl. No. 18/422,591 dated Dec. 20, 2024, 42 pages.

Deloitte, "Tech Trends 2021", Delotte Insights, https://www2.deloitte.com/content/dam/insights/articles/7023_TT-Machine-data-revolution-feeding-the-machine/DI_2021-TT-machine-data-revolution.pdf, last accessed Nov. 2, 2023, 21 pages.

Anadiotis, George, "5 Technology Trends for the Roaring 20s, Part 2: AI, Knowledge Graphs, Infinity and Beyond", On-line publication on ZD NET, https://www.zdnet.com/article/5-technology-trends-for-the-roaring-20s-part-2-aiknowledge-graphs-infinity-and-beyond/, Jan. 16, 2020, 9 pages.

McMahan et al., "Federated Learning: Collaborative Machine Learning without Centralized Training Data", Google Blog, https://ai.googleblog.com/2017/04/federated-learning-collaborative.html, Apr. 6, 2017, 5 pages.

TensorFlow, "TensorFlow Federated: Machine Learning on Decentralized Data", Online Available at URL: https://www.tensorflow.org/federated, last accessed Aug. 28, 2023, 4 pages.

schema.org, Company website https://schema.org/, last accessed Aug. 28, 2023, 1 page.

schema.org, "IoT and Schema.org: Getting Started", https://schema.org/docs/iot-gettingstarted.html, last accessed Sep. 19, 2023, 15 pages.

Maguire et al., "A Metadata-Based Architecture for User-Centered Data Accountability", Electron Markets, Online available at https://link.springer.com/article/10.1007/s12525-015-0184-z, vol. 25, 2015, pp. 155-160.

Chavarukattil, et al. "Generative Artificial Intelligence Driven Self-healing Agent for Medical Devices" U.S. Appl. No. 18/749,679, filed Jun. 21, 2024, 37 pages.

(56) References Cited

OTHER PUBLICATIONS

"Dual Ultrasound Switching Using Analog Switches Ed—Darl Kuhn", ip.com, ip.com Inc., West Henrietta, NY, US;; Oct. 10, 2014 (Oct. 10, 2014), XP013165092, ISSN: 1533-0001.
Docker M. F.: "Doppler ultrasound monitoring technology", BJOG: An International Journal of Obstetrics and Gynaecology, vol. 100, No. s9, Mar. 1, 1993 (Mar. 1, 1993), pp. 18-20, XP093279166, GB, ISSN: 1470-0328, DOI: 10.1111/j.1471-0528.1993.tb10630.x.
EP application 25150797.6 filed Jan. 8, 2025—extended Search Report issued Jun. 2, 2025; 11 pages.
Extended European Search Report received for European Patent Application Serial No. 25150798.4 dated Jun. 16, 2025, 7 pages.
Notice of Allowance received for U.S. Appl. No. 18/426,572 dated Nov. 19, 2025, 8 pages.
Non Final Office action received for U.S. Appl. No. 18/426,977 dated Sep. 17, 2025, 21 pages.
Anonymously, "Direct Digital Synthesis Based Ultrasound Doppler Transducer", ip.com, ip.com Inc., IPCOM000224998D, Jan. 18, 2013, 10 pages.
Extended European Search Report received for European Patent Application Serial No. 25150330.6 dated Jul. 2, 2025, 14 pages.
Notice of Allowance received for U.S. Appl. No. 18/426,977 dated Feb. 26, 2026, 5 pages.
Communication pursuant to Article 94(3) EPC received for EP Patent Application Serial No. 25150330.6 dated May 21, 2026, 06 page.

* cited by examiner

300

HYBRID TIME DOMAIN MULTIPLEXING AND FREQUENCY DOMAIN MULTIPLEXING CONFIGURATIONS FOR ULTRASOUND FETAL HEART RATE MONITORING SYSTEMS

TECHNICAL FIELD

This application relates to doppler ultrasound based fetal heart rate (FHR) monitoring systems, and more particularly to hybrid time domain multiplexing (TDM) and frequency domain multiplexing (FDM) configurations for improving depth coverage and power reduction while ensuring coexistence in a doppler-based ultrasound fetal monitoring system.

BACKGROUND

Fetal heart rate (FHR) monitoring is a routine procedure during pregnancy check-ups and labor to ensure the baby's health. It helps detect changes in FHR that may indicate distress or other issues, prompting appropriate medical intervention if necessary.

A doppler-based FHR monitoring system is a non-invasive FHR monitoring system that utilizes the Doppler effect to detect changes in as well as the absolute value of the FHR. The Doppler effect is a change in frequency or wavelength of a wave (in this case, ultrasound waves) when the source of the wave and the observer are in relative motion. In the context of FHR monitoring, the Doppler effect is used to detect and measure the heartbeat. A fetal sensor device (FSD) with an ultrasound transducer is placed on the mother's abdomen. The transducer emits sound waves (ultrasound waves) that travel through the mother's tissues and into the uterus. When these ultrasound waves encounter the fetal heart, they are reflected back toward the transducer. Due to the motion of the fetal heart (which beats rhythmically), the frequency of the reflected waves is slightly shifted (Doppler shift) compared to the emitted waves. The Doppler-based monitoring system detects these shifts and calculates the fetal heart rate (FHR) based on the repetitive frequency changes. The results are displayed on a monitor device or printed on a chart, allowing healthcare providers to assess the fetal heart rate and its variability.

Conventional doppler-based FHR monitoring systems utilize wired communication between the FSD and the monitor device. Wireless doppler-based FHR systems have been developed to provide greater mobility and convenience compared to traditional wired FHR systems. What sets a wireless FSD apart is its ability to transmit the FHR data wirelessly to the monitor device, thus eliminating physical wires or cables for connecting the FSD to the monitoring device.

While wireless FSDs offer numerous benefits, they also introduce new issues and challenges. One issue with wireless FSDs is power consumption. In particular, wireless FSDs rely on batteries for power and prolonged monitoring sessions, especially during extended labor, can drain the batteries, potentially leading to interruptions in monitoring. (In addition, both wired and wireless FSDs are susceptible to interference and crosstalk in scenarios in which two or more FSDs are used to respectively monitor two or more fetuses of the mother at the same time (e.g., as applied to monitoring twins, triplets, quadruplets, and so on). Accordingly, techniques for minimizing power consumption and crosstalk, while optimizing system performance are desired.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described that provide hybrid TDM and FDM configurations for improving depth coverage and power reduction while ensuring coexistence in a doppler-based ultrasound fetal monitoring system (FMS).

According to an embodiment, a FMS is provided that comprises a plurality of fetal sensor devices (FSDs) respectively comprising ultrasound transducers and configured to measure signals representative of one or more fetal parameters of a single fetus using doppler-based ultrasound technology, the one or more fetal parameters comprising at least one of, FHR, fetal movement, or fetal depth, and wherein each of the FSDs are configurable to operate using either a FDM mode or a TDM mode. The FMS further comprises at least one memory that stores computer-executable components, and at least one processor that executes the computer-executable components stored in the at least one memory. The computer-executable components comprise a context component that determines context information regarding an operating context of the FMS, the context information comprising a number of the FSDs activated for monitoring a corresponding number of fetuses of a single mother in association with positioning of the FSDs on an external body of the single mother (e.g., the mother's abdomen). The computer-executable components further comprise a configuration component that configures respective operating modes of the FSDs based on the context information and in accordance with a configuration protocol that varies the respective operating modes under different operating contexts of the FMS, the respective operating modes comprising the FDM mode and the TDM mode.

In various implementations, the configuration protocol further achieves one or more defined optimization criteria under the different operating contexts, the one or more defined optimization criteria selected from the group consisting of: minimizing power consumption by the FSDs, minimizing crosstalk between the FSDs (e.g., in scenarios in which two or more FSDs are used to simultaneously monitor two or more corresponding fetuses of the same mother), and achieving requisite depth coverage.

In some implementations, the configuration protocol comprises a hybrid configuration wherein based on the number of the FSDs being greater than one, the configuration component configures at least a first one of the FSDs to operate in the FDM mode and at least a second one of the FSDs to operate in the TDM mode, thereby enabling operating corresponding ultrasound transducers of the respective FSDs at lower pulse repetition rate (PPR) relative to a PRR restricted by a configuration in which the respective ones of the FSDs operate using the same operating mode, the same operating mode being either the FDM mode or the TDM mode. In other implementations, the configuration protocol comprises another hybrid configuration wherein based on the number of the FSDs being greater than two, the configuration component configures at least a first one of the FSDs to operate in the FDM mode and at least a second one of the FSDs to operate in the TDM mode, thereby enabling operating corresponding ultrasound transducers of the respective ones of the FSDs at lower pulse repetition rate (PPR) relative to a PRR restricted by a configuration in which the respective ones of the FSDs operate using the same operating mode, the same operating mode being either the FDM mode or the TDM mode.

In some implementations, the configuration protocol comprises switching configuring the respective ones of the FSDs between the FDM mode and the TDM mode based on the different operating contexts, wherein the different operating contexts correspond to different numbers of the respective ones of the FSDs activated for the monitoring of the corresponding number of fetuses of the single mother. In various implementations, the context information further comprises respective anatomical positions of the fetuses within the womb of the single mother relative to positions of the respective ones of the FSDs as positioned on the external body of the single mother, and wherein the different operating contexts account for different ones of the respective anatomical positions. The configuration component can further reconfigure one or more operating parameters of the respective FSDs based on a change to the operating context as determined by the context component, the one or more operating parameters comprising the operating mode, either the FDM mode or the TDM mode, the PRR, and the operating frequency.

In one or more implementations, the configuration component is stored and executed by a monitor device, wherein the monitor device and the FSDs are communicatively coupled via one or more wired or wireless communication technologies. With these implementations, the monitor device can configure the operating modes and operating parameters of the respective FSDs via corresponding configuration command signals sent to the respective FSDs. Additionally, or alternatively, each of the FSDs can intelligently configure their respective operating modes (e.g., either FDM or TDM) and operating parameters (e.g., PRR, signal frequency, etc.) based on feedback information regarding the operating context of the FMS (e.g., indicating the number of transducers being used and the relative positions (e.g., depths) of the respective fetuses to which they are configured to monitor). Some or all of this feedback information may be determined by one or more of the FSDs themselves and communicated between the FSDs themselves (e.g., in a peer-to-peer fashion) and/or determined by the monitor device and communicated to the respective FSDs.

In some embodiments, elements described in connection with the disclosed systems can be embodied in different forms such as a computer-implemented method, a computer program product, or another form.

DETAILED DESCRIPTION

Figure 1:
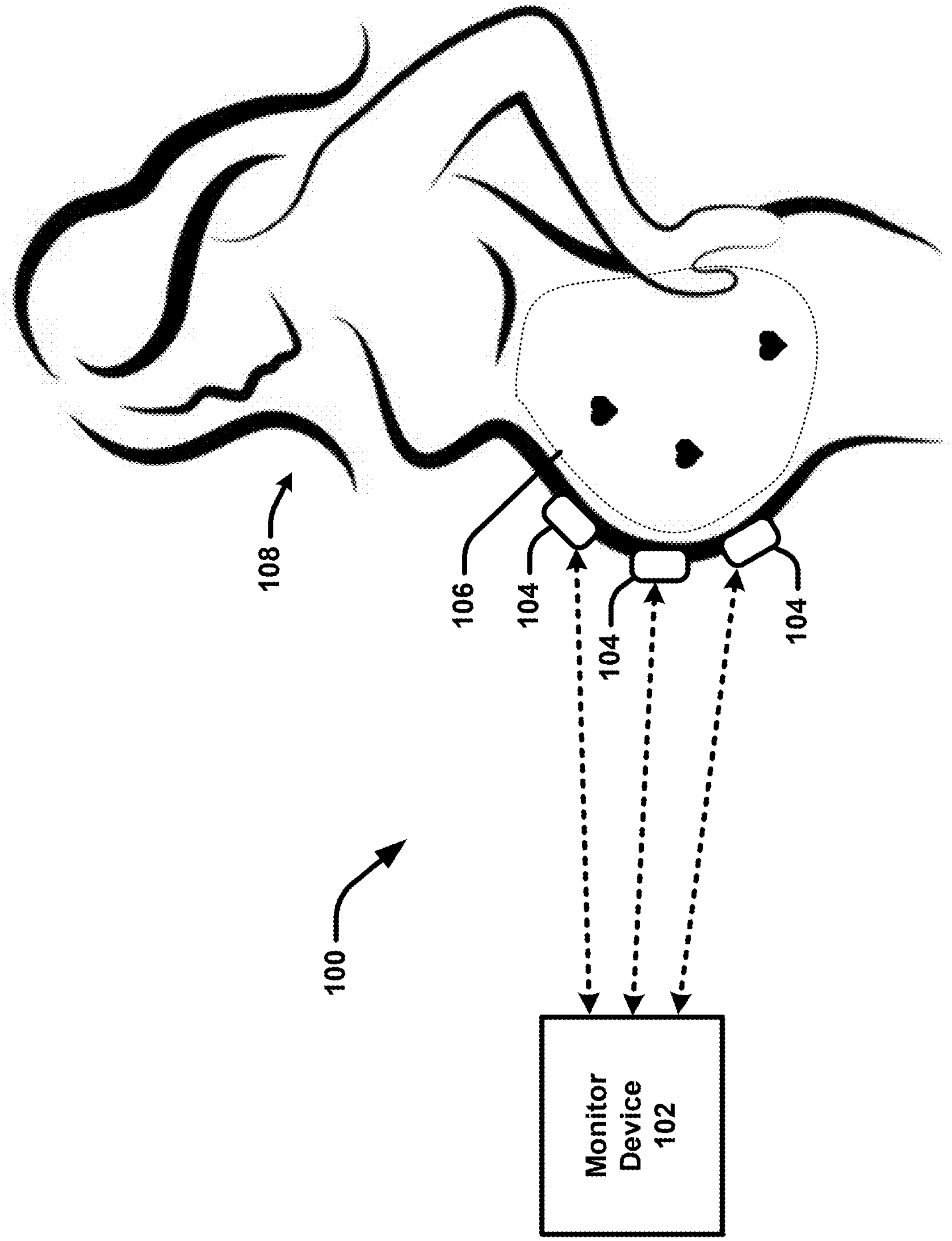
FIG. 1 presents an example fetal monitoring system (FMS) in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The subject disclosure provides systems, computer-implemented methods, apparatus and/or computer program products that facilitate hybrid TDM and FDM configurations for a doppler-based ultrasound fetal monitoring system (FMS). In various embodiments, the doppler-based FMS system utilizes a plurality of fetal sensor devices (FSDs) respectively comprising ultrasound transducers to simultaneously measure one or more fetal parameters (e.g., FHR, fetal movement, fetal depth, and other potential parameters) of a corresponding number of fetuses of the same mother (e.g., as applied to monitoring twins, triplets, quadruplets, etc.), wherein each FSD is configured to measure the one or more fetal parameters for a single fetus using doppler-based ultrasound technology. With these embodiments, in scenarios in which two or more FSDs are used at the same time to respectively measure fetal parameters for two or more fetuses of the same mother, crosstalk and interference between the respective FSDs becomes an issue. In this context, crosstalk refers to the interference or overlap of signals between different FSDs, or more specifically, one FSD picking up the signals of another FSD, primarily due to frequency aliasing effects in the demodulation process. As described in greater detail infra, the hybrid TDM and FDM configurations facilitate reduced power consumption by the respective FSDs and enable the capability to monitor two or more fetuses of the same mother simultaneously without signal confusion or crosstalk while also improving depth coverage and sensitivity.

Time domain multiplexing (TDM) and frequency domain multiplexing (FDM) are two techniques that can be used in doppler-based fetal heart rate (FHR) monitoring systems to distinguish between signals from different FSDs and reduce interference between signals in scenarios in which two or more FSDs are used simultaneously. In TDM mode, the ultrasound signals emitted by the respective transducers of the FSDs are multiplexed as a function of time (e.g., transmitted and thus received at different time sequences), and the demodulation process ensures that each FSD only decodes the reflected doppler shift on signals received on its time sequence. In FDM mode, each of the transducers operates at a distinct carrier frequency, and the corresponding demodulation process ensures that the FSD only decodes the reflected doppler shift on its carrier frequency.

However, both TDM and FDM suffer from different drawbacks which limit the performance of the FHR monitoring system. In particular, when the FSDs are time domain multiplexed, as the number FSDs increases, the amount of time each sensor is able to function with distinguishable signals multiplexed in time decreases. This causes a drop in sensitivity and depth coverage of the respective FSDs. In this context, the sensitivity refers to the ability to accurately detect and measure the fetal parameters of a fetus (e.g., FHR, fetal movement, fetal depth and other potential parameters), and the depth coverage refers to the sensing depth or distance range of the FSD, typically measured as a function of the distance from the surface of the mother's abdomen toward the internal body of the uterus. In this regard, the depth coverage required for a FSD as applied to monitoring FHR and other fetal parameters corresponds to the relative distance between the fetal heart and the position of the FSD as placed on the external body of the mother (e.g., typically the abdominal surface), which varies from patient to patient, as well as the number of fetuses. With FDM, the signals between different transducers can be more easily distinguished from one another because the respective transducers are operated at different carrier frequencies. However, to avoid incidences of crosstalk and interferences with FDM, the carrier frequencies must be separated reasonably and the difference between any two not a multiple of the pulse repetition rate (PRR).

In doppler ultrasound fetal monitoring, the pulse repetition rate (PRR) refers to the number of ultrasound pulses emitted per a defined time period (e.g., every 1.0 microsecond (μs), every 1.0 second (s), or another defined time period). The PRR is typically measured in kilohertz (kHz). The PRR is an important parameter because it determines how frequently the ultrasound waves are sent into the body and the duration of time any reflected waves may be received by the transducer. For example, the transducer emits a number of ultrasound waves over a transmit (Tx) period, followed by a receive (Rx) period in which the reflected ultrasound waves may be received by the transducer. During a monitoring session, the transducer continuously operates by alternating between transmit and receive periods. The PRR controls the number of sound waves emitted over the transmit period and the duration of the receive period. During the transmit period, the emitted sound waves travel into the body toward a targeted fetal heart. When one or more of the soundwaves reach the targeted fetal heart, they are reflected back to the transducer.

Although a higher PRR allows for more frequent updates of the fetal parameter signal, as the PRR increases, the receive period decreases. As the duration of the receive period decreases, the ability of the transducer to receive reflected waves from the targeted tissue (e.g., fetal heart tissue as applied to FHR monitoring) at greater depths decreases, as these reflected waves require a longer time to reach and bounce back to the transducer from tissues at greater depths, creating a blind zone at certain depths beyond a threshold depth. To this end, the PRR can control the depth coverage of the FSD. For example, in scenarios in which the fetal heart is positioned within the womb at a depth greater than about 15.0 centimeters (cm) from the abdominal surface of the mother, a low PRR, such as about 2.0 kHz, is preferable to be able to detect FHR data. In this regard, a lower PRR helps with improving depth coverage because the receive periods can be longer which allows more travel time for the ultrasound signals by allowing them to go to wider range of depths and subsequently be received and processed. An additional benefit of working at lower PRR is the reduction in power consumption that is possible due to lowering the number of Tx transmit instances in a given time. This is even more beneficial for extending battery life in embodiments in which the FSDs are wireless, where battery life dictates the duration of continuous monitoring possible between FSD changes or battery charges.

However, for coexistence of n transducers using only the FDM mode on a single mom, the PRR must be at least n kHz. So, for monitoring triplets on a mother (n=3), the PRR can be a minimum of 3.0 kHz for FDM. In particular, to avoid incidences of crosstalk and interferences between signals of two or more transducers when each of the transducers are operating in FDM, the different carrier frequencies must be separated reasonably and the difference between any two not a multiple of the PRR. In one example with three transducers on FDM, assume the three carrier frequencies are set apart by 11 kHz, so the difference between any two transducer carrier frequencies is either 11 kHz or 22 kHz. In this example, the PRR can be 3.0 kHz or higher. In triplets or a higher number of fetus scenarios, it is more likely that one or more of the fetuses are located deeper down from the surface of the abdomen; hence a greater depth coverage would be beneficial, which is more readily available if the PRR is at 2.0 kHz. In addition, with TDM, sensitivity goes down with an increasing number of sensors as the PRR is reduced.

With this context in mind, the disclosed subject matter provides a hybrid of TDM and FDM approach for a doppler-based ultrasound FMS system which can allow operation with lower PRR for the FSDs, giving the extra depth coverage and lowering the power consumption of the FSDs while also minimizing crosstalk in scenarios in which two or more FSDs are used for simultaneously monitoring a corresponding number of fetuses of the same mother. In one or more embodiments, a FMS is provided that comprises a plurality of FSDs respectively comprising ultrasound transducers and configured to measure signals representative of one or more fetal parameters of a single fetus using doppler-based ultrasound technology, the one or more fetal parameters comprising at least one of, FHR, fetal movement, or fetal depth, and wherein each of the FSDs are configurable to operate using either the FDM mode or the TDM mode. In various embodiments, each of the FSDs can be communicatively coupled to a monitor device via one or more wired and/or wireless communication technologies and configured to provide raw and/or processed signal data indicating the corresponding fetal parameters (e.g., FHR, fetal movement, fetal depth, and optionally other relevant information) to the monitor device for rendering over the course of a fetal monitoring session.

The FMS can further determine and monitor the operating context of the FMS 100 and intelligently configure the operating parameters of the respective FSDs 104 based on the operating context and in accordance with a configuration protocol that varies and tailors the operating parameters of the respective FSDs based on different operating contexts of the FMS. The operating parameters can include (but are not limited to) the operating modes of the respective FSDs, either FDM or TDM, the carrier frequencies of the respective FSDs and the PRRs of the respective FSDs. To this end, the different operating contexts can account for different numbers of FSDs activated for monitoring a corresponding number of fetuses of a single mother in association with positioning of the respective FSDs on an external body of the single mother (e.g., typically the abdomen). The different operating contexts can also account for respective depths of the fetal heart or hearts being monitored by the respective FSDs. In some implementations, the different operating contexts can also account for other contextual variables such as the intended duration of the monitoring session, the current power levels of the respective FSDs, and various others, as discussed infra.

The configuration protocol can further define and/or control the optimal operating configurations (e.g., the respective operating parameters) for the respective FSDs under the different operating contexts, wherein the optimal operating configurations are determined or inferred to achieve one or more defined optimization criteria, including at least one of, minimizing power consumption by the FSDs, minimizing crosstalk between two or more FSDs, and achieving the requisite depth coverage. To this end, the particular operating parameters of each active FSD will vary based on the number of FSDs being utilized and the corresponding number of fetuses being monitored, the depths of the respective fetuses, and optionally other contextual factors of the FMS. The FMS can further dynamically reconfigure the particular operating parameters of the respective FSDs during a monitoring session based on changes to the operating context over the course of the monitoring session. For example, the FMS can intelligently switch the operating mode of a FSD between the FDM mode and the TDM mode based on addition or removal of one or more FSD over the course of the monitoring session, based on new information regarding respective depths of the one or more fetuses, based on changes to the positions of the one or more fetuses, based on monitored performance measures of sensitivity, crosstalk, signal quality, and other potential contextual factors.

In accordance with the disclosed techniques, at least some of the optimal operating configurations can include a hybrid configuration wherein based on the number of the active FSDs being greater than one (e.g., as applied to monitoring twins, triplets, quadruplets, and so on), the FMS configures at least one of the FSD to operate using the FDM mode and at least a second one of the FSDs to operate using the TDM mode. For example, in some embodiments, if there are only two FSDs in use, the FMS can configure the respective FSDs in FDM mode at different frequencies, thus minimizing crosstalk, while also configuring the PRR to be a low value (e.g., about 2.0 kHz or greater), thereby providing optimal depth coverage. However, in scenarios in which three FSDs are used for monitoring triplets, a hybrid FDM and TDM approach can be used. For example, two of the FSDs can be configured to operate using TDM mode at a first frequency (F1) and at low PRR (e.g., of about 2.0 kHz or greater) and the third FSD can be configured to operate using the FDM mode at a second frequency (F2) and the low PRR. In this scenario, the first two FSDs can operate in TDM mode and quickly pick up two of the fetal hearts that are closer to the abdominal surface and the third FSD can automatically operate in the FDM mode with larger depth coverage, thus helping the clinical workflow to place the third FSD for the triplet, which is expected to be relatively at larger depths than the first two fetuses. The operating modes of each of the FSDs can thus be dynamically configured and reconfigured by the FMS to adapt to different usage scenarios. In some embodiments, using two carrier frequencies, and two FSDs operating in TDM at each frequency, the FMS can be extended to monitor quadruplets at a low PRR (e.g., of about 2.0 kHz or greater), thus providing reduction in power consumption while also minimizing crosstalk.

Embodiments of systems and devices described herein can include one or more machine-executable (i.e., computer-executable) components or instructions embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. These computer/machine executable components or instructions (and others described herein) can be stored in memory associated with the one or more machines. The memory can further be operatively coupled to at least one processor, such that the components can be executed by the at least one processor to perform the operations described. In some embodiments, the memory can include a non-transitory machine-readable medium, comprising the executable components or instructions that, when executed by a processor, facilitate performance of operations described for the respective executable components. Examples of said and memory and processor as well as other suitable computer or computing-based elements, can be found with reference to FIG. 11 (e.g., processing unit 1104 and system memory 1106 respectively), and can be used in connection with implementing one or more of the systems or components shown and described in connection with FIG. 1, or other figures disclosed herein.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 presents an example FMS 100 in accordance with one or more embodiments of the disclosed subject matter. The FMS 100 includes a monitor device 102 and a plurality of FSDs 104. Each FSD 104 can include an ultrasound transducer configured to measure signals representative of one or more fetal parameters of a single fetus using doppler-based ultrasound technology in association with placement of the respective FSDs 104 on the external body of the mother 108. For example, the FSDs 104 are typically placed on the external surface of the abdomen to allow the mother 108 to comfortably lay on her back during the monitoring session. However, in some implementations, the FSDs 104 may be positioned on the side body and/or the mother's back. The FSDs 104 may be held in place using straps or another suitable mechanism once the FSDs have been placed in optimal positions on the mother's body in which they are accurately picking up corresponding targeted fetal hearts.

The one or more fetal parameters measured by the respective FSDs 104 can include, but are not limited to, FHR, fetal movement, and fetal depth. Over the course of a fetal monitoring session, the FSDs 104 can be configured to send raw and/or processed signal data representative of the one or more fetal parameters to the monitor device 102 for additional processing and/or rendering via one or more suitable output devices of the monitor device 102 (e.g., a display, a speaker, etc.). To this end, each of the FSDs 104 can include an ultrasound transducer that generates and transmits acoustic pulses (i.e., ultrasound waves) directed toward a fetus positioned within the womb 106 in association with placement thereof on the external body of the mother 108. The ultrasound transducer emits ultrasound waves and receives reflected and ultrasound waves that are reflected from one or more targeted tissues within the womb 106, which in this context includes a fetal heart. More particularly, the ultrasound transducer comprises a transmitter/receiver element, typically comprising one or more crystals and/or a piezoelectric element, that generates ultrasound waves when an electric current is applied to it. The transmitter/receiver element also receives the reflected ultrasound waves. The transmitter/receiver element is integrated within a head portion of the FSD housing that is placed in direct contact with the mother's skin. Due to the motion of the fetal heart (which beats rhythmically), the frequency of the reflected ultrasound waves is slightly shifted (Doppler shifted) compared to the emitted waves. This shift is proportional to the beating velocity of the fetal heart surface/membrane. These shifts can be detected and used to calculate the fetal heart rate (FHR), fetal movement and fetal depth based on the repetition rate of the frequency changes using one or more algorithms executed by signal processing unit (e.g., a computer-executable signal processing unit).

In some embodiments, each of the FSDs 104 can include signal processing functionality to detect the doppler shifted signals from the fetus, demodulate and condition the data (e.g., amplify, filter, digitize, etc.), compute the fetal parameters (e.g., FHR, fetal movement and/or fetal position/depth) and send the fetal parameters to the monitor device 102 for rendering thereof to one or more clinicians (e.g., via a display, a speaker, and/or another suitable output device) and/or for additional processing thereof. In other embodiments, some or all of the signal processing can be performed by the monitor device 102. For example, each of the FSDs 104 can be configured to send raw doppler shifted signals to the monitor device 102 for signal processing and/or send partially processed signals (e.g., demodulated signals, digitized signals, etc.) to the monitor device 102 which in turn can process the raw or partially processed signals to calculate the FHR, fetal movement, fetal position/depth, and so on.

The monitor device 102 and the respective FSDs 104 can be communicatively coupled via any suitable wired or wireless communication technology. For example, the monitor device 102 and the respective FSDs 104 can respectively be configured to communicate information between one another using any suitable wireless communication technology, such as but not limited to: Bluetooth™, Wireless Fidelity (Wi-Fi), near field communication (NFC), Zigbee™, Z-wave™, infrared (IR), ultra-wideband (UWB), body area network (BAN) communication technologies, medical body area network (MBAN) communication technologies, cellular, and various other existing and foreseen wireless communication technologies. In some embodiments, the wireless communication technology can include a wireless communication technology tailored for performance under water to enable usage of the FSDs 104 for monitoring FHR data in water birth scenarios. Additionally, or alternatively, one or more of the FSDs 104 and the monitor device 102 may be communicatively coupled to one another via one or more wired communication technologies.

In the example embodiment illustrated in FIG. 1, three FSDs 104 are being used in the context of monitoring triplets, wherein each fetus is represented by a heart symbol depicted within the womb 106 of the mother 108. However, the FMS 100 can be tailored to different usage scenarios involving different numbers of fetuses and thus different numbers of FSDs 104, one or for each fetus. For example, the FMS 100 can be tailored in association with using a single FSD 104 to monitor a single fetus, two FSDs 104 to respectively monitor two fetuses, three FSDs 104 to respectively monitor three fetuses, four FSDs 104 to respectively monitor four fetuses, and so on.

Each FSD 104 can also include suitable hardware and/or software that enables the operations described with respect to each FSD 104 as disclosed herein. For example, in some embodiments, each FSD 104 can include an onboard power source (e.g., one or more batteries or another suitable power source), a memory that and processor that that enable onboard signal processing functionality and other computer-executable functions described herein, wireless or wired communication hardware and software that enable wired and/or wired communication between the FSD 104 and the monitor device 102, one or sensors that provide for sensing various parameters associated with the FSD, the mother 108 and/or the fetus (e.g., proximity sensors, contact sensors, temperature sensors, motion sensors, etc.), and other suitable hardware and/or software described with reference to FIG. 6.

In various embodiments, each of the FSDs 104 are adapted to operate their respective ultrasound transducers using both TDM mode and FDM mode, and the particular operating mode of each FSD 104 for a given usage scenario can be dynamically configured and tailored based on the operating context of the FMS 100 in accordance with a configuration protocol that varies respective operating modes of the FSDs under different operating contexts. The configuration protocol can also control additional operating parameters of the FSDs 104 including but not limited to, the PRR, the carrier frequency, and TDM sequencing between two or more FSDs simultaneously operating in TDM mode, wherein the configuration protocol varies and tailors these operating parameters for different operating contexts.

In particular, the different operating contexts can account for different numbers of the FSDs 104 activated and applied to the mother 108 for monitoring a corresponding number of fetuses. The different operating contexts can also account for respective anatomical positions of the fetuses within the womb 106 of the mother relative to positions of the corresponding ones of the FSDs 104 as positioned on the external body of the mother (i.e., the respective depths of the fetuses within the womb 106 or the distances between the respective FSDs 104 and the corresponding fetal hearts to which they are coupled). In some embodiments, the different operating contexts can also account for other contextual parameters, such as but not limited to, the intended duration of the fetal monitoring session (e.g., a relatively short duration as applied to check-up sessions, a relatively longer duration as applied to continuous monitoring during labor, and so on), the power/battery level or levels of the respective FSDs, monitored measures of crosstalk, monitored measures of signal quality, monitored measure of sensitivity, and others).

To this end, the configuration protocol employed by the FMS 100 can define and/or control the optimal operating parameters (e.g., operating mode, with FDM mode or TDM mode, PRR, operating frequency, and optionally others) for the different operating contexts of the FMS in a manner that achieves one or more defined optimization criteria under the different operating contexts, the one or more defined optimization criteria selected from the group consisting of: minimizing power consumption by the respective FSDs 104, minimizing crosstalk between the respective FSDs (e.g., in scenarios involving two or more FSDs used simultaneously), and achieving requisite depth coverage. To facilitate this end, the FMS 100 can determine and monitor the operating context of the FMS 100 and configure the operating parameters of the respective FSDs 104 according based on the configuration protocol. The FMS 100 can also dynamically reconfigure the operating parameters of the FSDs 104 over the course of a monitoring session based on changes to the operating context (e.g., based on addition and/or removal of FSDs, based on changes to the position of the fetal heart or hearts being monitored, based on changes in power/battery levels of the FSDs 104, based on changes in sensitivity, changes to measure of crosstalk/interference, changes to measure of signal quality, and so on).

In various embodiments, to optimize depth coverage, the configuration protocol can control setting the PRR of the respective FSDs 104 to a low value, preferably about 3.0 kHz or less, regardless of whether the FSDs 104 are operating in TDM or FDM and regardless of the number of the FSDs activated for simultaneously monitoring a corresponding number of fetuses of the same mother. As noted above, the PRR refers to the number of ultrasound pulses emitted per a defined time period, or more particularly, as the rate of repetition of the Tx and Rx period. An additional benefit of working at lower PRR is the reduction in power consumption that is possible due to lowering the number of Tx transmit instances in the given time period. This is even more beneficial for extending battery life of the FSDs 104 in embodiments in which the FSDs 104 are wirelessly coupled to monitor device 102 (and/or powered by onboard batteries as opposed to receiving power from a wired power source) and in operating contexts involving continuous monitoring over extended periods of time (e.g., during labor or another continuous monitoring scenario), where battery life dictates the total duration of continuous monitoring possible between FSD changes or battery charges.

Figure 2:
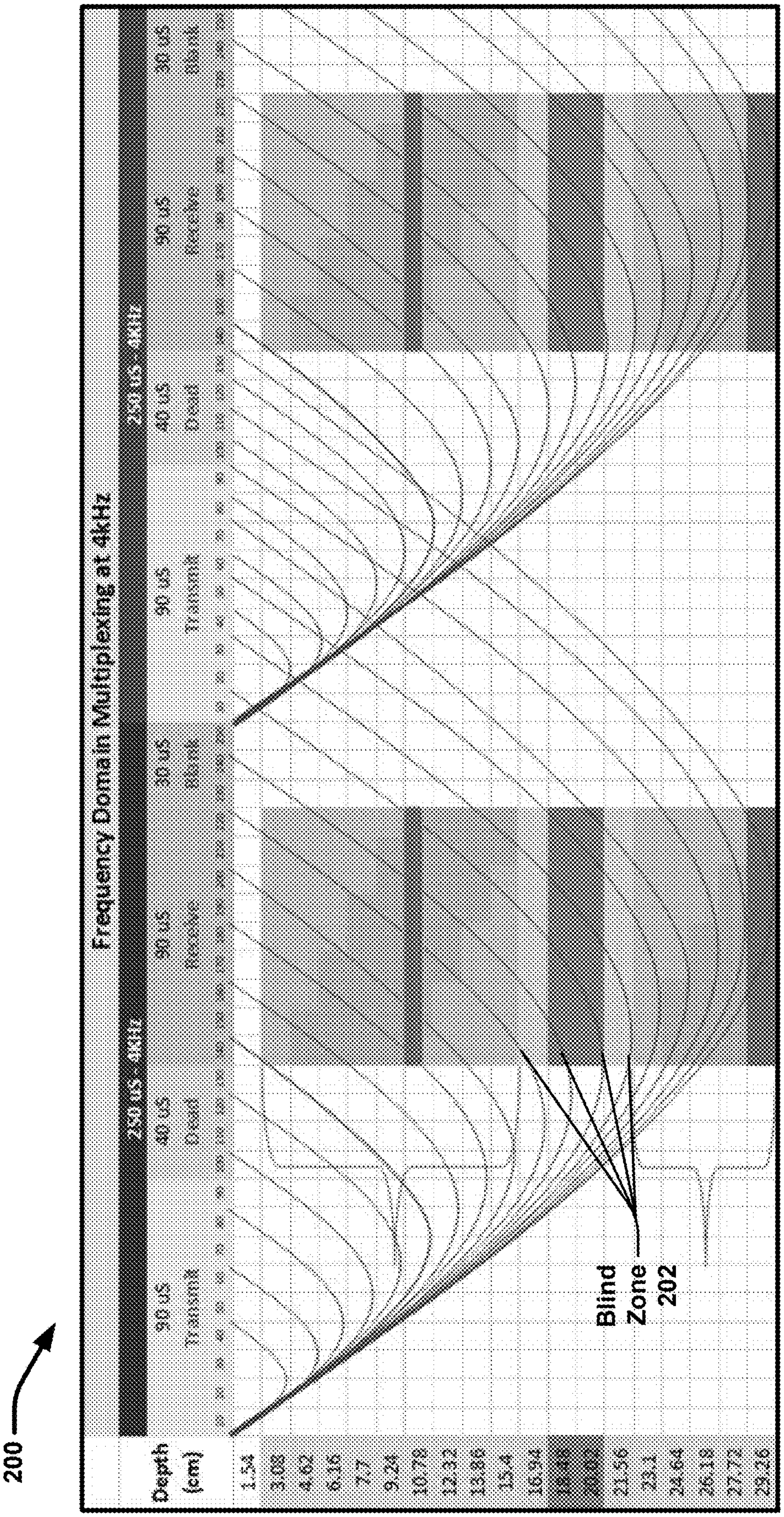
FIG. 2 presents a chart illustrating performance of an example fetal sensor device (FSD) operating in FDM mode at a PRR of 4.0 kilohertz (kHz), in accordance with one or more embodiments of the disclosed subject matter.
Figure 3:
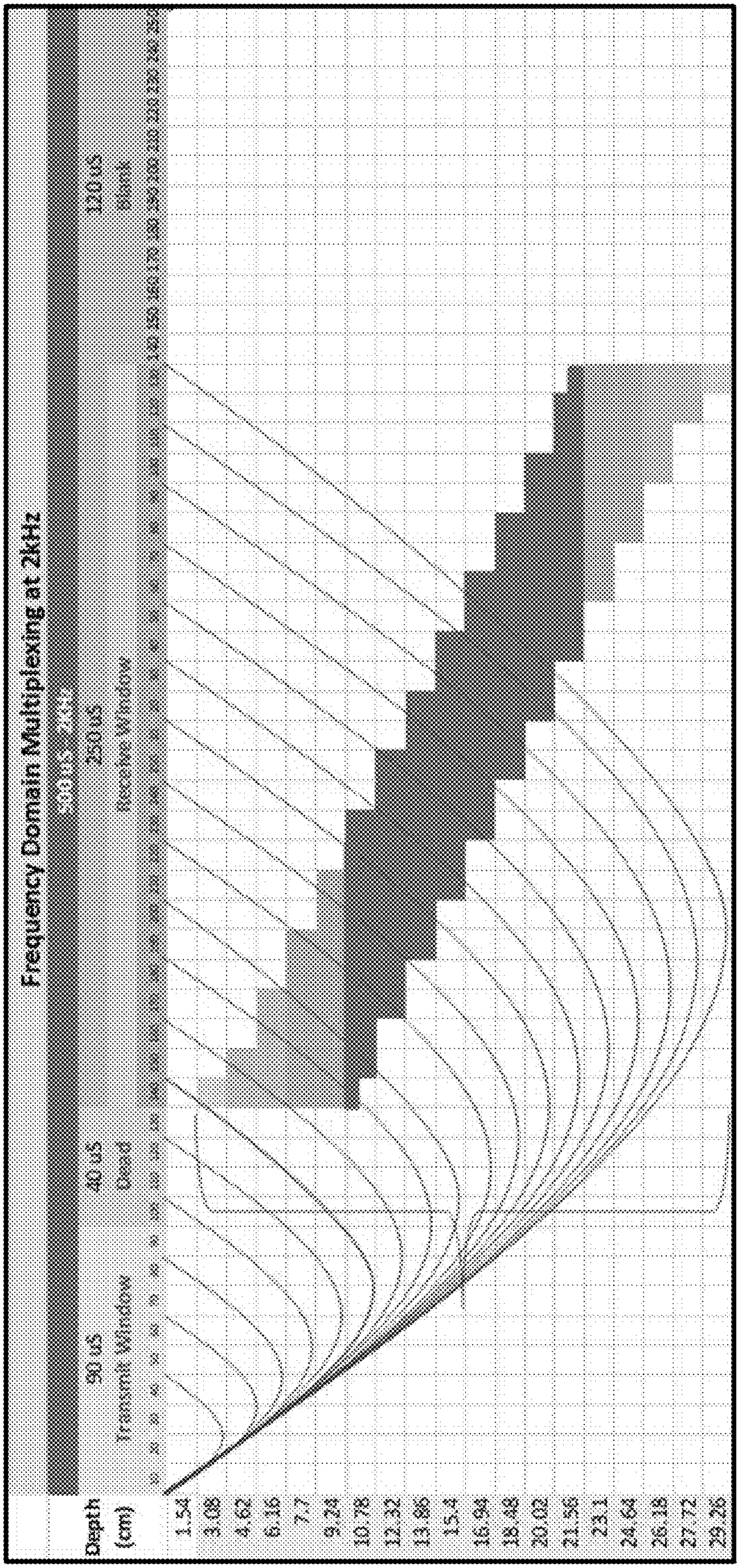
FIG. 3 presents a chart illustrating performance of an example FSD operating in FDM mode at a PRR 2.0 kHz, in accordance with one or more embodiments of the disclosed subject matter.

In this regard, FIG. 2 presents a chart 200 illustrating performance of an example FSD 104 operating in FDM mode at a PRR of 4.0 kilohertz kHz every 250 μs, in accordance with one or more embodiments of the disclosed subject matter. FIG. 3 presents a chart 300 illustrating performance of the FSD 104 operating in FDM mode at a PRR 2.0 kHz every 500 μs, in accordance with one or more embodiments of the disclosed subject matter.

With reference to FIGS. 1-3, as illustrated in charts 200 and 300, in doppler ultrasound based fetal monitoring, the ultrasound transducer of the FSD 104 operates in a cyclical manner with repeating duty cycles every defined time period (e.g., every 250 μs at the PRR of 4.0 kHz with respect to chart 200 and every 500 μs at the PRR of 2.0 kHz with respect to chart 300). Each duty cycle involves a transmit (Tx) period, followed by a dead period, followed by a receive (Rx) period and a blank period. During the transmit period, the transducer emits ultrasound waves in a pulsed manner that travel into the body toward a targeted fetal heart. As the emitted ultrasound waves encounter tissues in the body, they are reflected back toward the transducer. Each pulse takes x amount of time to reach the targeted fetal heart and the speed of the ultrasound pulses dictates the depth at which target tissues can be detected. Charts 200 and 300 represent the progression of the Tx waves (depth versus time). The horizontal lines represent the depths at which potential reflections from tissues and heart movement can occur. The end points of the parabolic curves then represent the time at which the corresponding reflection returns back to the ultrasound transducer.

In this regard, the ultrasound transducer can only measure the FHR based on those signals which are bounced back and received during the receive period. As illustrated in chart 200 and 300, many of the pulsed waves are not received during the immediate receive period following the transmit period, as some are reflected back by other tissues in the body besides the targeted fetal heart and reflected back during the dead period (e.g., a wait period in which the transducer device does not transmit or receive). In addition, as illustrated in chart 200, some of the ultrasound waves that travel deeper into the body are reflected back toward the transducer and reach the transducer after the receive period has passed (e.g., during the blank period, another wait period in which the transducer does not transmit or receive, or during the next transmit period). For example, as illustrated in chart 200, those ultrasound waves that reach depths between about 16 cm and 22 cm are reflected back to the transducer after the immediate receive period has ended, creating a blind zone 202 in coverage between those depths when the PRR is 4.0 kHz.

In this regard, as the distance between the transducer and the targeted tissue increases, the duration of time needed for the ultrasound waves to reach the targeted tissue and be reflected back to the transducer also increases. Accordingly, if the receive window is shorter than this duration of time, some of the ultrasound sound waves reflected from the targeted tissue may not be detected by the transducer. As illustrated via comparison of charts 200 and 300, as the PRR decreases (e.g., from 4.0 kHz for chart 200 to 2.0 kHz for chart 300), the allowable time for the receiving window increases, thereby enabling the transducer to detect reflected ultrasound waves at greater depths. For example, as illustrated in chart 300, the longer receive window created based on the lower PRR of 2.0 kHz allows for sensing through depths all the way from about 3.0 cm to about 29 cm, thus eliminating the blind zone 202 established at the higher PRR of 4.0 kHz.

However, for coexistence of n transducers using only FDM on a single mom, the PRR must be at least n kHz. So, for monitoring triplets on a mother (n=3), the PRR can be a minimum of 3.0 kHz for FDM. In particular, to avoid incidences of crosstalk and interferences between signals of two or more FSDs 104 when each of the FSDs are operating in FDM mode, the different carrier frequencies must be separated reasonably and the difference between any two not a multiple of the PRR. In one example with three FSDs operating in FDM mode, assume the three carrier frequencies are set apart by 11 kHz, so the difference between any two transducer carrier frequencies is either 11 kHz or 22 kHz. In this example, the PRR is restricted to being 3.0 kHz or higher to avoid crosstalk. In triplets or a higher number of fetus scenarios, it is more likely that one or more of the fetuses are located deeper down from the surface of the abdomen; hence a greater depth coverage would be beneficial, which is more readily available if the PRR is less than 3.0 kHz. In addition, in preferred embodiments, the carrier frequencies of the respective FSDs 104 are restricted to low or narrowband frequencies, preferably less than 5.0 megahertz (MHz), more preferably less than 4.0 MHz, more preferably less than 3.0 MHz and even more preferably less than 2.0 MHz. For example, in some implementations, the configuration protocol can restrict the carrier frequencies that the respective FSDs 104 can operate using to a frequency range between about 1.0 MHz and about 2.0 MHz. Accordingly, the restricted frequency range limits the ability to reasonably separate the different frequencies of multiple FSDs as further constrained by the limitation that the difference between any two different carrier frequencies not a multiple of the PRR. Narrowband transducers are often used in doppler ultrasound for FHR monitoring due to their specific advantages in capturing and analyzing the doppler signals. For example, narrowband transducers within a specific frequency range (e.g., about 1.0 to about 5.0 MHz), allow for a more focused detection of the doppler signals related. This can result in a higher signal-to-noise (SNR) ratio, enhancing the accuracy of fetal heart rate measurements.

In one or more embodiments, in order to utilize a PRR less than 3.0 kHz for all three FSDs 104 as applied to monitoring triplets while also minimizing crosstalk and using narrowband frequencies (e.g., preferably less than 5.0 MHz, more preferably less than 4.0 MHz, more preferably less than 3.0 MHz and even more preferably less than 2.0 MHz), the configuration protocol of the FMS 100 can define a hybrid configuration for this operating context, wherein two of the FSDs can be configured to operate in TDM mode at a first frequency (F1) and the third FSD can be configured to operate in FDM mode at second frequency (F2) different from the first frequency, wherein the difference between the first and second frequency is not a multiple of the PRR. With this configuration in which the first two FSDs 104 are operating in TDM mode at the first frequency (F1) and the third FSD 104 operates at the second frequency (F2) in FDM mode, signal confusion can be avoided. At the same time, because all three FSDs can be configured to operate with a PRR of less than 3.0 kHz, power consumption is reduced as a result of requiring fewer transmit instances and thus reduced transmit power, while also increasing the depth coverage owing to the longer receive window afforded by the low PRR (of less than 3.0 kHz) of the third FSD 104. Thus, the combination of TDM and FDM helps overcome the limitations described for the individual methods.

As noted above, the particular operating mode (e.g., either TDM or FDM), PRR and carrier frequency of the FSDs 104 can be configured as tailored to different operating contexts of the FMS 100 and in accordance with a configuration protocol that varies and tailors these operating parameters for the different operating contexts in a manner that results in minimizing power consumption by the respective ones of the fetal sensor devices, minimizing crosstalk between the respective ones of the fetal sensor devices, and/or achieving requisite depth coverage under the constrained narrowband frequency range defined for the respective FSDs (e.g., preferably less than 5.0 MHz, more preferably less than 4.0 MHz, more preferably less than 3.0 MHz and even more preferably less than 2.0 MHz), and under the constraint that the different carrier frequencies must be separated reasonably and the difference between any two not a multiple of the PRR. In some embodiments, the configuration protocol can define different optimal operating configurations for the FSD operating parameters (e.g., respective operating modes, either TDM or FDM, the respective carrier frequencies, and the respective PRRs) under different defined operating contexts (e.g., wherein the different defined operating contexts account for different numbers of FSDs being used, respective depths of the corresponding fetus, and other contextual factors discussed herein). In some implementations of these embodiments, the FMS 100 can determine the current operating context of the FMS and configure the respective FSDs 104 in accordance with the particular operating parameters defined for the corresponding operating context.

Additionally, or alternatively, the configuration protocol can employ one or more defined optimization functions that can be used to determine the optimal operating parameters for the FSDs under a current operating context, wherein the one or more defined optimization functions account for different values for the contextual parameters (e.g., number of active FSDs, corresponding fetal depths, and other contextual factors disclosed herein), the optimization criteria defined above (e.g., minimizing crosstalk, minimizing power consumption, and achieving requisite depth coverage), and the constraints defined above (e.g., a narrowband frequency range constraint, and the constraint that the different frequencies must be reasonably separated and the difference between them not a multiple of the PRR). Still in other embodiments, the optimization protocol can employ a combination of both predefined optimal operating configurations for different operating contexts and allow for further tailoring or adjusting (e.g., reconfiguring) the operating parameters of the FSDs 104 relative to the defined optimal operating configurations in accordance with the one or more optimization functions based on monitored feedback regarding the depths of the fetuses being monitored, sensitivity of the respective FSDs, power/battery levels of the respective FSDs, signal quality, and other contextual variables.

To this end, the particular operating parameters of each active FSD 104 will vary based on the number of FSDs being utilized and the corresponding number of fetuses being monitored, the depths of the respective fetuses, and optionally other contextual factors of the FMS 100. The FMS 100 can further dynamically reconfigure the particular operating parameters of the respective FSDs during a monitoring session based on changes to the operating context over the course of the monitoring session. For example, the FMS can intelligently switch the operating mode of a FSD 104 between the FDM mode and the TDM mode based on addition or removal of one or more FSD over the course of the monitoring session, based on new information regarding respective depths of the one or more fetuses (e.g., in implementations in which the depths are determined and tracked), based on changes to the positions of the one or more fetuses, based on monitored indications of sensitivity, crosstalk, and other potential contextual factors.

In accordance with some embodiments of the disclosed techniques, at least one of the optimal operating configurations defined and/or controlled by the configuration protocol can include a hybrid configuration wherein based on the number of the active FSDs being greater than one (e.g., as applied to monitoring twins, triplets, quadruplets, and so on), the FMS 100 configures at least one of the FSDs 104 to operate using the FDM mode and at least a second one of the FSDs 104 to operate using the TDM mode. In other embodiments, at least one of the optimal operating configurations defined and/or controlled by the configuration protocol can include another hybrid configuration wherein based on the number of the active FSDs being greater than two (e.g., as applied to monitoring twins, triplets, quadruplets, and so on), the FMS 100 configures at least one of the FSDs 104 to operate using the FDM mode and at least a second one of the FSDs to operate using the TDM mode.

Figure 4:
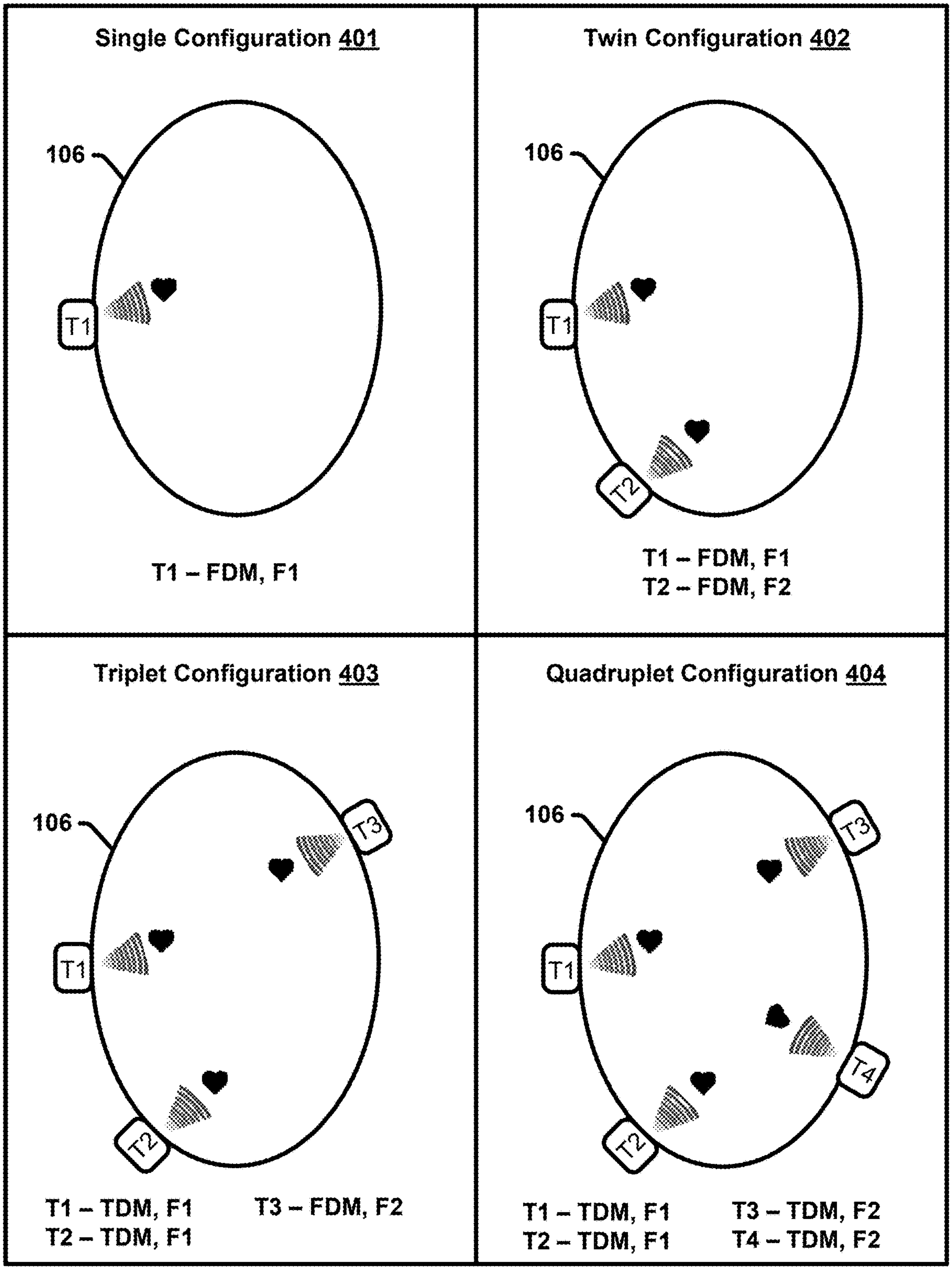
FIG. 4 presents example operating configurations of respective FSDs of a FMS under different operating contexts in accordance with one or more embodiments of the disclosed subject matter.

FIG. 4 presents some example operating parameter configurations for different FMS operating contexts that can be defined by the optimization protocol employed by the FMS 100, in accordance with one or more embodiments of the disclosed subject matter. With reference to FIG. 4 in view of FIGS. 1-3, FIG. 4 illustrates four example operating parameter configurations respectively corresponding to a single configuration 401 (e.g., for monitoring a single fetus within the womb 106), a twin configuration 402 (e.g., for simultaneously monitoring two fetuses within the womb 106), a triplet configuration 403 (e.g., for simultaneously monitoring three fetuses within the womb 106), and a quadruplet configuration 404 (e.g., for simultaneously monitoring four fetuses within the womb 106). As illustrated in FIG. 4, the FSDs 104 are respectively labeled T1, T2, T3 and T4 (wherein the letter "T" is used to refer to the respective ultrasound transducers of the FSDs 104). To this end, each FSD is used to monitor one or more fetal parameters for a single fetus (e.g., one FSD 104 per fetus), represented by a heart symbol within the womb 106.

In one or more embodiments, as applied to the single configuration 401, the configuration protocol can direct the FMS 100 to configure the single FSD (e.g., corresponding to T1) to operate in FDM mode at a first frequency, F1. With these embodiments, the first frequency F1 can vary as controlled under the defined narrowband frequency constraints of the configuration protocol (e.g., preferably between about 1.0 MHz and 3.0 MHz). Continuing with the single configuration 401, in some implementations, the single configuration can also set the PRR of the FSD to be a low PRR (e.g., about 3.0 kHz or less), thereby minimizing power consumption while also providing high depth coverage. However, in other implementations, the configuration protocol can direct the FMS 100 to increase or decrease the PRR based on the relative position or depth of the fetus and optionally other contextual factors, as determined over the course of the monitoring session. For example, in implementations in which the depth or distance between the fetal heart and the transducer (T1) is less than a threshold distance (e.g., about 16 cm or less), the configuration protocol can direct the FMS to configure the FSD with a higher PRR (e.g., 3 kHz, 4 kHz, etc.) that provides the requisite depth coverage for the threshold distance. With these implementations, the FSD 104 and/or the monitor device 102 can determine and track the depth of the fetal heart using various techniques. In another example, the configuration protocol may also direct the FMS to configure the single FSD with a higher PRR (e.g., greater than a threshold PRR value, such as 2.0 kHz) in scenarios in which the increased power consumption attributed to the higher PRR is not an issue. For example, the FMS 100 may configure the single FSD with a higher PRR in scenarios in which the capacity of the battery of the FSD is sufficient to enable operation of the transducer device for the duration of the monitoring session, which can vary depending on the context of the monitoring session (e.g., shorter durations for check-ups as opposed to longer durations for labor). This is also a possibility with wired FSDs where the power comes from a wired power source, thus rendering the power consumption issue void.

In one or more embodiments, as applied to the twin configuration 402, each of the two FSDs (e.g., corresponding to T1 and T2) can be configured to operate in FDM mode, with the first FSD (e.g., T1) at a first frequency, (F1) and the second FSD (e.g., T2) at a second frequency (F2) different from the first frequency. With these embodiments, to minimize or prevent crosstalk between the respective FSDs, the first and second carrier frequencies must be separated reasonably and the difference between them two not a multiple of the PRR (as defined by as a constraint of the configuration protocol). In various embodiments, the first carrier frequency (F1) and the second carrier frequency (F2) can be set to different frequencies within the defined narrowband frequency constraints of the configuration protocol (e.g., preferably between about 1.0 MHz and 3.0 MHz) and such that the frequency difference between them is not a multiple of the PRR. In some implementations of the twin configuration 402, both the first and second FSDs (e.g., T1 and T2) can be configured to operate with a low PRR (e.g., less than about of 3.0 kHz), thereby minimizing power consumption while also providing high depth coverage (e.g., up to about 29 cm). However, in other implementations, the PRR of each FSD can be increased (or decreased) based on the relative positions of the corresponding fetuses to which they are coupled, and other potential contextual parameters of the monitoring session, as described above with respect to the single configuration.

In one or more embodiments, as applied to the triplet configuration 403 wherein three FSDs 104 are used, the configuration protocol can direct the FMS 100 to configure two of the FSDs (e.g., T1 and T2) to operate in TDM mode at a first frequency, (F1), and to configure the third FSD (e.g., T3) to operate in FDM mode at a second frequency (F2), (i.e., an example hybrid configuration). For the first and second FSDs operating in TDM mode, the time sequence of the respective FSDs can be synchronized with one another such that their respective signals are differentiable from one another in the time domain. For example, the start time of the Tx periods of the first and second transducers operating in TDM can be shifted relative to each other in time. With these embodiments, although three different FSDs are being used simultaneously, only two different carrier frequencies are used, and thus under the constraint that the difference between the two different frequencies (F1) and (F2) must be not a multiple of the PRR, the PRR of all three FSDs can be set to a value less than 3.0 kHz, thus enabling better depth coverage while also enabling the different frequencies to be narrowband frequencies within a defined low frequency range (e.g., between 1.0 and about 3.0 MHz). For example, in some implementations of the triplet configuration 403, all three of the FSDs can be configured to operate with a PRR of 2.0 kHz, thereby minimizing power consumption while also providing high depth coverage (e.g., up to about 29 cm). With these embodiments, the one FSD operating in FDM mode will have higher depth coverage relative to the two FSDs operating in TDM mode and without any blind zones. Thus, in some implementations, the FMS 100 can dynamically configure the FSD focused on the deepest fetal heart of the three in the FDM mode.

However, in other implementations, the PRR of each of the three FSDs can be increased (or decreased) based on the relative positions of the corresponding fetuses and the context of the monitoring session, as described above with respect to the single configuration. In some embodiments of the hybrid configuration, the particular one of the three FSDs configured in the FDM mode can correspond to the FSD applied for monitoring the one of three fetuses positioned at the greatest depth from the abdominal surface. For example, in some embodiments, upon beginning a monitoring session for a triplet scenario, the FMS 100 can initially configure any two of the FSDs 104 to operate in the TDM mode at the first frequency (F1) and the third FSD to operate in the FDM mode at the second frequency (F2). Based on feedback received and/or determined over the course of the monitoring session indicating the relative distances of each fetus to each FSD, the FMS 100 can thereafter reconfigure the operating modes of the respective FSDs as needed such that the FSD picking up the fetal heart rate at the greatest distance is configured in the FDM mode at the second frequency F2.

In this regard, in some embodiments in which the depths of the fetal hearts are being tracked, the FMS 100 can dynamically reconfigure the FSDs 104 to operate either in the TDM mode or the FDM mode, dynamically reconfigure the PRR of the FSDs and/or dynamically reconfigure the operating frequency of the FSDs. For example, in some implementations, as applied to a triplet scenario, the operating protocol can direct the FMS 100 to switch over to a pure FDM configuration wherein all three FSDs operate using FDM at a PRR of 3.0 kHz or higher, based on the depths of the respective fetal hearts being less than a threshold depth. For example, in a triplet scenario, if all three fetal hearts are at moderate depths (e.g., less than about 16 cm), each of the transducers could move to a PRR of 3.0 kHz and pure FDM configuration with three different carrier frequencies respectively separated from one another and the difference between any two carrier frequencies not a multiple of the PRR. On the other hand, if two of the fetal hearts are closer to the surface and one is deep, the three FSDs could move to the hybrid TDM/FDM configuration illustrated in the example triplet configuration 403.

In one or more embodiments, as applied to the quadruplet configuration 404, the configuration protocol can direct the FMS to configure all four of the FSDs (e.g., T1, T2, T3 and TF) to operate in TDM mode, with two of the FSDs (e.g., T1 and T2) operating at a first frequency (F1) and another two of the FSDs (e.g., T3 and T4) operating at a second frequency (F2). With these embodiments, the PRR can be set to less than 3.0 kHz (e.g., preferably about 2.0 kHz), thereby allowing for optimal depth coverage while also configuring the first and second frequencies under the constraint that the difference between the two frequencies is not a multiple of the PRR and within the defined narrowband frequency range (e.g., between about 1.0 MHz and about 3.0 MHz). Cross-talk can be avoided owing to the usage of two different frequencies while multiplexing in the time domain. In this case, since each of the four FSDs are in TDM mode, there will be the blind zones in the depth coverage. This is because in TDM mode, the Rx periods are limited to only the immediate Rx. For example, each of the FSDs operating in the same frequency (e.g., T1 and T2, or T3 and T4) would do one round of Tx and Rx each independently in time (e.g., corresponding to Tx1-Rx1 and Tx2-Rx2), wherein one of the FSDs cannot receive during Rx2, hence the reduction in depth. In some embodiments, the configuration protocol can include another full TDM mode configuration applicable to monitoring five or six fetuses simultaneously. With this scenario, the fifth and/or sixth FSD can be configured to operate in the TDM mode yet at a third carrier frequency (F3), wherein the three different carrier frequencies are reasonably separated and the difference between any two of the three different carrier frequencies is not a multiple of the PRR.

It should be noted the configuration protocol employed by the FMS 100 is not limited to the different example configuration illustrated in FIG. 4. In this regard, various alternative configurations are envisioned wherein the respective operating modes (e.g., either TDM or FDM), the PRR, and frequencies of each FSD 104 can vary and include different combinations of these parameters as tailored to account for the number of fetuses being monitored, the depths of the fetuses, the power demands of the monitoring session, and other contextual factors that can change over the course of the monitoring session.

In some embodiments, the monitor device 102 can determine and configure the operating parameters (e.g., operating mode (either TDM or FDM), PRR, carrier frequency, TDM sequencing, etc.) of the respective FSDs 104 as tailored for to the current operating context of the FMS system 100. For example, the monitor device 102 can determine context information regarding the current operating context of the FMS 100 (e.g., the number of FSDs activated and applied to the mother, the relative positions/depths of the corresponding fetuses being tracked, and other contextual parameters disclosed herein). The monitor device 102 can further determine the optimal operating parameters for the respective FSDs based on the context information and the configuration protocol described herein. The monitor device 102 can further send (e.g., wirelessly and/or via wired communication lines) configuration commands to the respective FSDs 104 identifying or indicating their respective operating parameters and instructing the respective FSDs 104 to operate in accordance with their respective operating parameters. With these embodiments, based on reception of the configuration commands, the FSDs 104 can be configured to apply the received operating parameters.

Additionally, or alternatively, each of the FSDs 104 can intelligently configure their respective operating parameters (e.g., operating mode, either FDM or TDM), PRR, signal frequency, etc.) in accordance with the configuration protocol described herein based on context information regarding the current operating context of the FMS 100. For example, in some implementations, the FSDs 104 themselves can determine the context information themselves and be respectively configured to apply the configuration protocol described herein in association with determining the optimal operating parameters for the current operating context and configuring themselves accordingly (e.g., the configuration protocol can be defined in memory of the respective FSDs 104). Additionally, or alternatively, the monitor device 102 can determine some or all of the context information, communicate the context information to the respective FSDs 104, and wherein the FSDs 104 are configured to respectively apply the configuration protocol described herein in association with determining the optimal operating parameters for the current operating context and configuring themselves accordingly (e.g., the configuration protocol can be defined in memory of the respective FSDs 104). Still in other embodiments, some or all of the context information and/or the optimal determined operating parameters for the current operating context may be determined by the monitor device 102 and/or the FSDs 104 themselves and communicated between the FSDs 104 in a peer-to-peer fashion.

Figure 5:
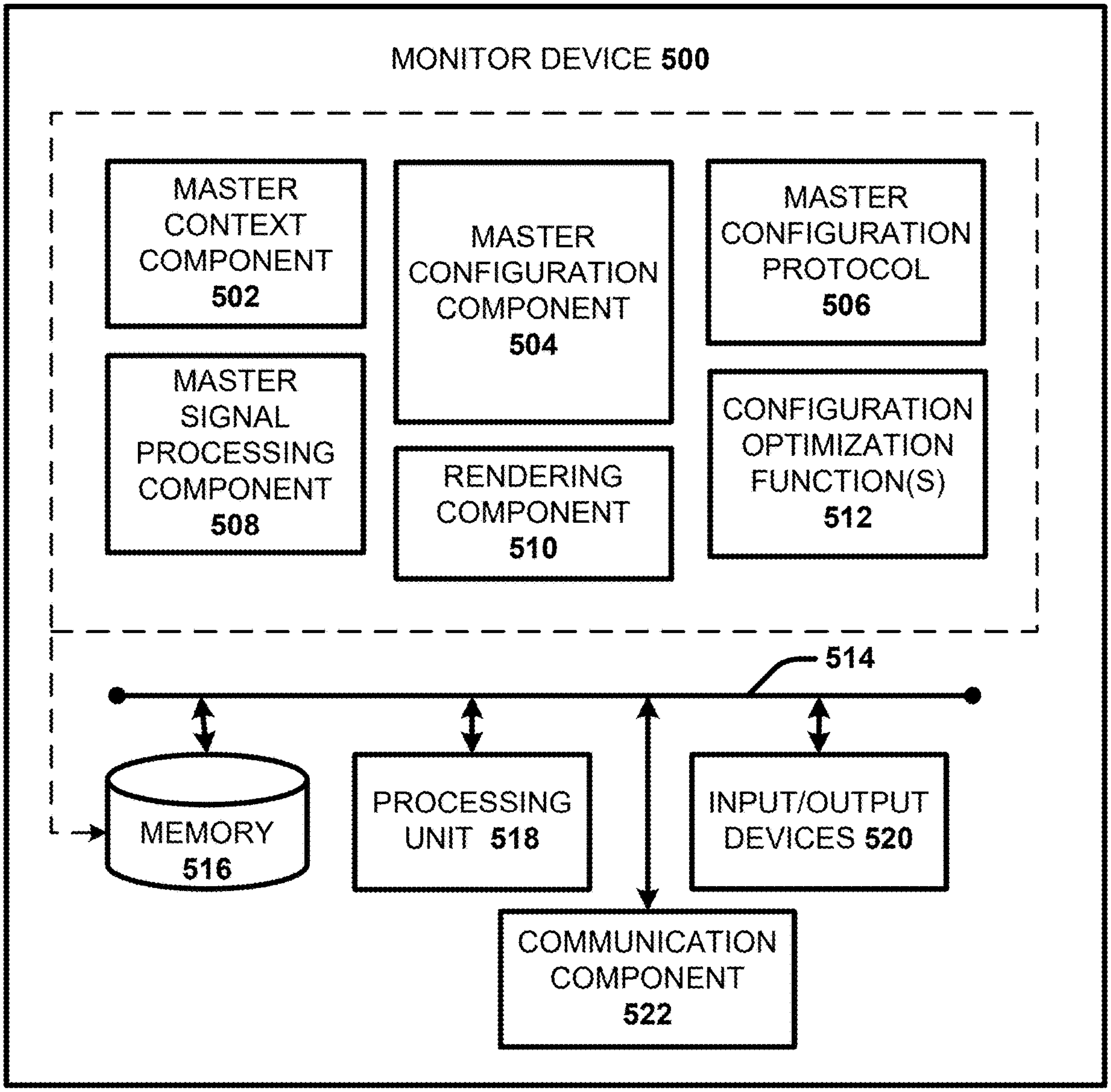
FIG. 5 illustrates a block diagram of an example, non-limiting monitor device of a FMS in accordance with one or more embodiments of the disclosed subject matter.

FIG. 5 illustrates a block diagram of an example, non-limiting monitor device 500 in accordance with one or more embodiments of the disclosed subject matter. With reference to FIGS. 1-5, in various embodiments, monitor device 500 can include or correspond to monitor device 102 of FMS 100. The monitor device 500 can include or correspond to any suitable computing device that can perform operations described with reference to monitor device 102 and FIGS. 1-4 and additional figures described herein. For example, the monitor device 500 can include or correspond to one or more computing devices, machines, virtual machines, computer-executable components, datastores, and the like that may be communicatively coupled to one another either directly or via one or more wired or wireless communication frameworks.

To this end, monitor device 500 can include at least one memory 516 that stores machine-executable or computer-executable components or instructions embodied within one or more machines (e.g., embodied in one or more computer-readable storage media associated with one or more machines), and at least one processing unit 518 that executes the computer-executable components stored in the at least one memory 516. These computer-executable components or instructions can include (but are not limited to) master context component 502, master configuration component 504, master configuration protocol 506, master signal processing component 508, rendering component 510 and configuration optimization functions 512. Examples of said and memory and processing unit as well as other suitable computer or computing-based elements, can be found with reference to FIG. 11 (e.g., processing unit 1104 and system memory 1106 respectively), and can be used in connection with implementing one or more of the systems or components shown and described in connection with FIG. 11, or other figures disclosed herein.

Monitor device 500 can further include one or more input/output devices 520 to facilitate receiving user input and rendering data (e.g., via rendering component 510) to users in association with usage of FMS 100. In various embodiments, the input/output devices 520 can include a display monitor via which the monitor device 500 renders (e.g., via rendering component 510) processed ultrasound signal data measured by the active FSDs 104 over the course of a fetal monitoring session indicating one or more fetal parameters of the corresponding fetuses being monitored (e.g., FHR data, fetal movement data, and/or fetal position/depth data). For example, over the course of a fetal monitoring session, the monitor device 500 may render visual data (e.g., via a display monitor) that represents the heart rates of the respective fetuses being monitored in real-time (e.g., displayed in beats per minute), visual data that represents one or more measures of fetal movement in real-time, visual data indicating respective depths/positions of the fetal hearts as tracked in real-time, and so on. In another example, the monitor device 500 may also display visual data representing the patterns of the fetal hearts tracked over time.

In some implementations, the processed ultrasound signal data may be received from the respective FSDs 104 (e.g., the FSDs can be configured to perform signal processing of the doppler shifted ultrasound signals to determine/calculate the fetal parameters using corresponding algorithms and send the fetal parameters to the monitor device 500). Additionally, or alternatively, the FSDs 104 can be configured to send the monitor device 500 raw or partially processed ultrasound signal data (e.g., demodulated, de-multiplexed, amplified, digitized, etc.) and the monitor device 500 can be configured to perform signal processing of the raw or partially processed doppler shifted ultrasound signals (e.g., via master signal processing component 508) to determine/calculate the one or more fetal parameters using corresponding algorithms. For example, the master signal processing component 508 can track the respective operating parameters of each of the FSDs 104 and calculate the corresponding fetal parameters based on the raw or partially processed doppler shifted signals accordingly. The input/output devices can also include a speaker via which the rendering component 510 may render doppler audio representative of one or more fetal parameters over the course of the monitoring session (also affected by crosstalk, depth, etc.). Suitable examples of the input/output devices 514 are described with reference to FIG. 11 (e.g., input devices 1128 and output device 1136).

The information rendered via the monitor device 500 (e.g., via rendering component 510 and one or more suitable output devices) is not limited to data representing the monitored fetal parameters (e.g., FHR, fetal position/depth, and/or fetal movement). In this regard, any information associated with the FSDs 104 (e.g., generated by, stored by, etc.) and/or the monitor device 500 (e.g., generated by, stored by, etc.) may be rendered via the monitor device 500. For instance, additional examples of information that may be rendered via the monitor device 500 can include, but is not limited to, any of the context information described herein (e.g., pertaining to the operating context of the FMS), alarms, notifications, and information identifying the configuration settings of the respective FSDs. For example, in various embodiments, the monitor device 500 can be configured to detect issues or potential issues associated with a monitored fetus based on values of the one or more parameters being indicative of an issue or potential issue. The monitor device 500 can further generate and render (e.g., via the output device or another connected device) suitable notifications or alarms regarding detected issues or potential issues.

Monitor device 500 can also include a communication component 522 that includes or corresponds to hardware and/or software that enables wired and/or wireless communication between the monitor device 500 and the FSDs 104 using any suitable wired or wireless communication technology. In some implementations, the communication component 522 can also enable wired and/or wireless communication between the monitor device 500 and other external devices using any suitable wired or wireless communication technology. Monitor device 500 can further include a system bus 515 that couples the memory 516, the processing unit 518, the input/output devices 520 and the communication component 522 to one another.

In one or more embodiments, the master context component 502 can determine and/or receive (e.g., from the respective FSDs 104) context information regarding the operating context of the FMS 100. The master context component 502 can further regularly or continuously monitor the operating context of the FMS 100 and determine changes or updates to the context information in real-time or substantially real-time. As described above, the context information can include (but is not limited to), information identifying the number of active FSDs 104 applied to the mother 108 for monitoring a corresponding number of fetuses of the mother and information identifying or indicating respective depths of the corresponding fetuses (i.e., the relative distance between an FSD 104 as positioned on the external body of the mother and a corresponding fetal heart as positioned within the womb 106). The mechanism via which the master context component 502 determines the number of active FSDs 104 can vary. For example, in some implementations, the master context component 502 can detect when an FSD 104 has been activated for a monitoring session (e.g., turning on and/or entering an active fetal sensing mode) based on reception of an activation signal from the FSD 104 and/or when an FSD 104 is placed on or near the abdomen of the mother 108 based on reception of a corresponding application signal from the FSD 104 (e.g., as determined by the FSD 104 using one or more contact sensors, using one or more proximity sensors, or the like). For instance, in some scenarios in which the mother has two or more fetuses, the clinical workflow typically involves individually activating each FSD 104 at time, placing the FSD on the mother's abdomen in association with applying gel, moving the FSD about the mother's abdomen until the FSD 104 picks up a fetal heart of one of the fetuses and then setting the FSD 104 at that position. Thereafter, another FSD is activated and applied to the mother in the same manner in association with detecting another fetal heart, and so on. In accordance with this usage scenario, the master context component 502 can determine each time an FSD 104 is activated and applied to the same mother based on reception of information from the corresponding FSD 104 indicating its active status.

Information regarding respective depths of the fetal hearts being tracked can be determined based using one or more depth detection algorithms based at least in part on the doppler shifted signals transmitted and received by the ultrasound transducer of the FSD, the operating parameters of the FSD 104, and various other parameters (e.g., one or more or more measure of signal quality (e.g., SNR), as tracked over time.

In some embodiments, the context information can also include other contextual parameters, including but not limited to, the intended duration of the fetal monitoring session (e.g., a relatively short duration as applied to check-ups or a relatively longer duration as applied to continuous monitoring during labor, wherein information regarding the intended duration may be received by the master monitor device 500 via user input at the initiation of the fetal monitoring session), and information identifying current battery/power levels of the respective FSDs 104 (e.g., in implementations in which they are wireless devices). In some embodiments, the context information can also include one or more performance metrics of the FSDs 104, such as but not limited to, one or more measures of signal quality, one or more measure of crosstalk/interface, one or more measures of sensitivity and so on. The context information can also include the current operating parameters of the respective FSDs (e.g., current configuration settings with respect to operating mode, either FDM mode or TDM mode, carrier frequency and PRR).

In some embodiments, the master configuration component 506 can configure the operating parameters of the respective active FSDs 104 based on the operating context (e.g., based on the context information) of the FMS 100. With these embodiments, the master configuration component 506 can determine the optimal operating parameters (e.g., operating mode, either FDM mode or TDM mode, carrier frequency, and PRR) for the respective FSDs based on the current operating context (e.g., the number of active FSDs 104 and corresponding number of fetuses, the depths of the fetuses, and other contextual parameters discussed herein) and using the master configuration protocol 506 and/or one or more configuration optimization functions 512. The master configuration component 506 can further send configuration information to the respective FSD 104 identifying the particular operating parameters to be applied by each FSD 104 and instructing them to configure themselves accordingly. To this end, based on reception of the configuration information from the monitor device 500, the respective FSDs 104 can be configured to operate in accordance with their assigned operating parameters. In some embodiments, the master configuration component 506 can further reconfigure the operating parameters of one or more of the FSDs 104 (e.g., in accordance with the master configuration protocol 506 and/or the using the one or more configuration optimization functions 512) over the course of the monitoring session using updated configuration commands based on changes to the operating context.

In this regard, as noted above, the particular operating mode (e.g., either TDM or FDM), PRR and carrier frequency of the FSDs 104 can be configured as tailored to different operating contexts of the FMS 100 and in accordance with a configuration protocol (e.g., master configuration protocol 506 and/or local configuration protocol 606) that varies and tailors these operating parameters for the different operating contexts in a manner that results in minimizing power consumption by the respective ones of the FSDs 104, minimizing crosstalk between the respective ones of the FSDs 104, and/or achieving requisite depth coverage under the constrained narrowband frequency range defined for the respective FSDs (e.g., preferably less than 5.0 MHz, more preferably less than 4.0 MHz, more preferably less than 3.0 MHz and even more preferably less than 2.0 MHz), and under the constraint that the different carrier frequencies (e.g., when two or more carrier frequencies are used) must be separated reasonably and the difference between any two not a multiple of the PRR.

In some embodiments, the master configuration protocol 606 can define different optimal operating configurations for the FSD operating parameters (e.g., respective operating modes, either TDM or FDM, respective carrier frequencies or frequency ranges, and respective PRRs) under different defined operating contexts (e.g., wherein the different operating contexts account for different numbers of FSDs being used, respective depths of the corresponding fetus, and other contextual factors discussed herein). With these embodiments, the different defined optimal operating configurations can account for the different operating contexts, the optimization criteria and the constraints noted above. For example, in some implementations, the different optimal operating configurations can include and/or correspond to the example configurations illustrated in and described with reference to FIG. 4. The master configuration protocol 606 can also include or define context dependent variations to the optimal configurations illustrated in FIG. 4. Additionally, or alternatively, the master configuration component 504 can employ one or more configuration optimization functions 512 that can be used to determine the optimal operating parameters for the FSDs under a current operating context, wherein the one or more defined optimization functions account for different values for the contextual parameters (e.g., number of active transducers, fetal depths, etc.), the optimization criteria defined above (e.g., minimizing crosstalk, minimizing power consumption, and achieving requisite depth coverage), and the constraints defined above (e.g., narrowband frequency range constraints, and the constraint that the different frequencies must be reasonably separated and not a multiple of the PRR). Still in other embodiments, the master configuration component 504 can employ a combination of both predefined optimal operating configurations for different operating contexts and allow for further tailoring or adjusting (e.g., reconfiguring) the operating parameters of the FSDs relative to the defined optimal operating configurations based on monitored feedback regarding the depths of the fetuses being monitored, sensitivity of the respective FSDs, power/battery levels of the respective FSDs, signal quality, and other variables in accordance with the one or more optimization functions.

In this regard, it should be appreciated the optimal configuration parameters can vary from the configurations illustrated in FIG. 4 and be dynamically determined and adjusted by the master configuration component 504 (and/or corresponding local configuration components (e.g., local configuration component 604) executed by the respective FSDs 104), according to the number of fetuses being monitored, the relative depths of the fetuses, and the power demands of a monitoring session (e.g., wherein longer sessions equate to higher power demands), and other contextual parameters discussed herein, and under at least the following constraints: when different carrier frequencies are used, the difference between the respective carrier frequencies cannot be a multiple of the PRR, a defined narrowband carrier frequency range for the FSDs (e.g., preferably less than 5.0 MHz, more preferably less than 4.0 MHz, more preferably less than 3.0 MHz, and even more preferably less than 2.0 MHz), and under the constraint that the depth coverage enabled by the selected PRR is sufficient to enable detecting the targeted heart or hearts (e.g., depending on the depth or distance of the heart or hearts relative to the respective transducer devices). In some implementations of these embodiments, the master configuration component 506 can be configured to initially apply the respective configurations (e.g., as default configurations) illustrated in FIG. 4 based on the number of transducers activated. The master configuration component 506 can thereafter adjust the operating parameters of the respective FSDs based on the depth or depth of the fetal heart or hearts being tracked in accordance with the master configuration protocol 506 and/or the one or more configuration optimization functions 512). To this end, the optimal operating parameters (e.g., the individual and respective combinations of operating modes, PRRs and carrier frequencies) can be tailored to minimize or prevent crosstalk and interference when two or more transducers are used to simultaneously monitor two or more fetuses, provide requisite depth sensing (preferably when the transducer devices are positioned on the surface of mother's abdomen as opposed to the mother's back), and minimize power consumption.

In accordance some embodiments of the disclosed techniques, at least one of the optimal operating configurations defined and/or controlled by the master configuration protocol 506 and/or the one or more configuration optimization functions 512 can include a hybrid configuration wherein based on the number of the active FSDs being greater than one (e.g., as applied to monitoring twins, triplets, quadruplets, and so on), the master configuration component 504 configures at least one of the FSDs 104 to operate using the FDM mode and at least a second one of the FSDs 104 to operate using the TDM mode. In other embodiments, at least one of the optimal operating configurations defined and/or controlled by the master configuration protocol 506 can include another hybrid configuration wherein based on the number of the active FSDs being greater than two (e.g., as applied to monitoring twins, triplets, quadruplets, and so on), the master configuration component 504 configures at least one of the FSDs 104 to operate using the FDM mode and at least a second one of the FSDs to operate using the TDM mode.

Figure 6:
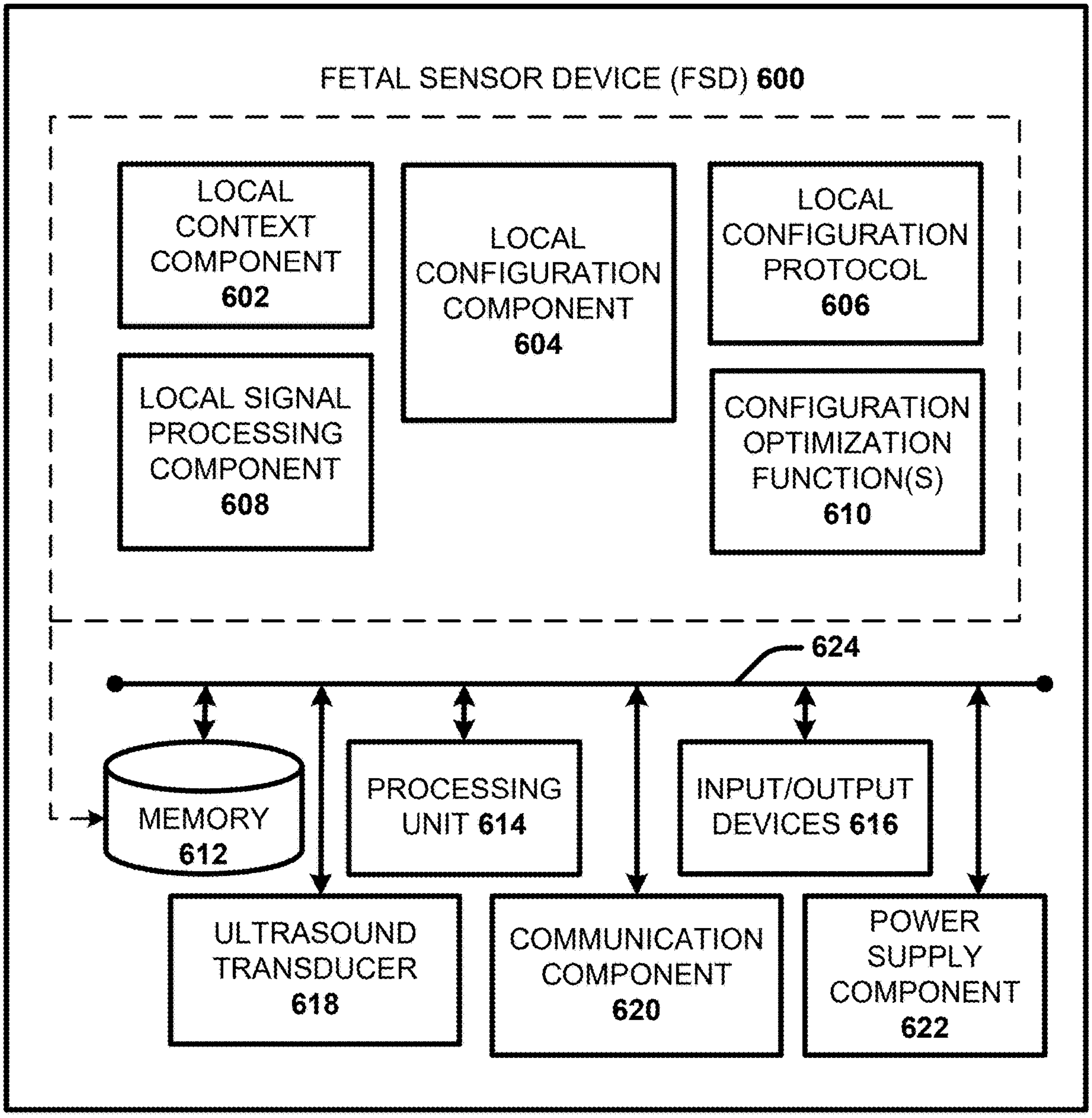
FIG. 6 illustrates a block diagram of an example, non-limiting FSD of a FMS in accordance with one or more embodiments of the disclosed subject matter.

FIG. 6 illustrates a block diagram of an example, non-limiting FSD 600 in accordance with one or more embodiments of the disclosed subject matter. With reference to FIGS. 1-6, in various embodiments, each of the FSDs 104 can include or correspond to FSD 600 (or vice versa). Repetitive description of like elements employed in respective embodiments is omitted for sake of brevity.

As mentioned with reference to FIG. 1, the FSD 600 can include or correspond to low power FSD configured to employ doppler-based ultrasound technology to continuously measure and provide information identifying or indicating one or more fetal parameters (e.g., FHR, fetal movement, fetal depth), and other information (e.g., context information) data to the monitor device 102. To this end, the FSD 600 can include an ultrasound transducer 618 that generates and transmits acoustic pulses (i.e., ultrasound waves) directed toward a fetus positioned within the womb 106 in association with placement thereof on an external body of the mother 108. The ultrasound transducer 618 further receives any reflected, doppler shifted signals from the fetus. The operating parameters of the ultrasound transducer 618, including (but not limited to), the operating mode (e.g., either TDM or FDM), the PRR and the carrier frequency, are further configurable. In some implementations, the FSD 600 can send (e.g., via communication component 620) the received raw doppler shifted signals to the monitor device 102 for signal processing (e.g., via the master signal processing component 508) to determine corresponding fetal parameters (e.g., fetal heart rate, fetal movement and/or depth). In other implementations, the FSD 600 can perform signal processing on the doppler shifted signals (e.g., via local signal processing component 608). For example, the local signal processing component 608 can demodulate and condition the data, amplify the data, digitize the data, and/or process the raw signals to determine one or more fetal parameters. With these embodiments, the FSD 600 can send the locally determined fetal parameters to the monitor device 102.

In this regard, in one or more embodiments, the FSD 600 can include at least one memory 612 that stores machine-executable or computer-executable components or instructions embodied within one or more machines (e.g., embodied in one or more computer-readable storage media associated with one or more machines), and at least one processing unit 614 that executes the computer-executable components stored in the at least one memory 612. These computer-executable components can include (but are not limited to) local context component 602, local configuration component 604, local configuration protocol 606, local signal processing component 608 and one or more configuration optimization functions 616. Examples of said and memory and processor as well as other suitable computer or computing-based elements, can be found with reference to FIG. 11 (e.g., processing unit 1104 and system memory 1106 respectively), and can be used in connection with implementing one or more of the systems or components shown and described in connection with FIG. 11, or other figures disclosed herein.

In various embodiments, the machine-executable or computer-executable components of the FSD 600 can perform same or similar operations described with respect to the corresponding components associated with the monitor device 500. For example, the local context component 602 can perform same or similar operations described with respect to master context component 502, the local configuration component 604 can perform same or similar operations described with respect to master configuration component 504, the local configuration protocol 606 and/or the optimization functions 610 can define and/or control the optimal operating parameters for the ultrasound transducer 618 in accordance with the information described with reference to the master configuration protocol 506 and the one or more optimization functions 512, and the local signal processing component 608 can perform same or similar operations described with respect to the master signal processing component 508. For example, in some embodiments, the local context component 602 can determine and monitor the operating context (e.g., operating context information) of the FMS 100 and the local configuration component 604 can configure the operating parameters of the FSD 600 (e.g., and/or more particularly the operating parameters of the ultrasound transducer 618) accordingly based on the local configuration protocol 606 and/or the one more configuration optimization functions 610. To this end, repetitive description of the same or similar functionalities of the respective components is omitted for sake of brevity.

In this regard, in some embodiments the FSD 600 can intelligently configure its operating parameters without instruction from the monitor device 500. In some implementations of these embodiments in which two or more FSDs 104 are actively used to simultaneously monitor a corresponding number of fetuses of the same mother, the respective FSDs (e.g., corresponding to FSD 600) can communicate with one another (e.g., in peer-to-peer fashion) in association with coordinating and configuring their respective operating parameters based on the operating context of the FMS 100. For example, the in some implementations, the first activated FSD can operate as the master controller in a manner described with reference to the monitor device and determine and/or control the operating parameters of itself and the other one or ones of the FSDs accordingly. Other variations involving a combination of communication of context information and operating parameter configurations between the respective FSDs 104 and/or the monitor device 102 are also envisioned.

In some implementations, the FSD 600 can include one or more input/output devices 616 to facilitate manually configuring the device and displaying data (e.g., configuration settings, battery level, processed FHR data, etc.) to users in association with usage of the FMS 100. Suitable examples of the input/output devices 616 are described with reference to FIG. 11 (e.g., input devices 1128 and output device 1136). The FSD 600 can also include a communication component 620 that includes or corresponds to hardware and/or software that enables wired and/or wireless communication between the FSD 600 and the monitor device (e.g., monitor device 102 or monitor device 500), and optionally enables wired and/or wireless communication between the FSD 600 and other FSDs activated for the monitoring session. In some embodiments (e.g., in which the FSD 600 corresponds to a wireless device), the FSD 600 can also include a power supply component 620 that corresponds to any suitable onboard power source (e.g., a rechargeable battery or another suitable power source). The FSD 600 can further include a system bus 628 that couples the memory 612, the processing unit 614, the input/output devices 616, the ultrasound transducer 618, the communication component 620 and the power supply component 622 to one another.

With reference to the machine/computer-executable components, in some embodiments, the monitoring component 602 can perform same or similar operations as the master monitoring component 502 yet on a local level as applied to the FHR data measured and/or determined for the particular fetus to which the transducer has been targeted to monitor. Likewise, the signal processing component 604 can perform same or similar operations as the master signal processing component 504 yet on a local level as applied to the FHR data measured and/or determined for the particular fetus to which the transducer has been targeted to monitor.

Figure 7:
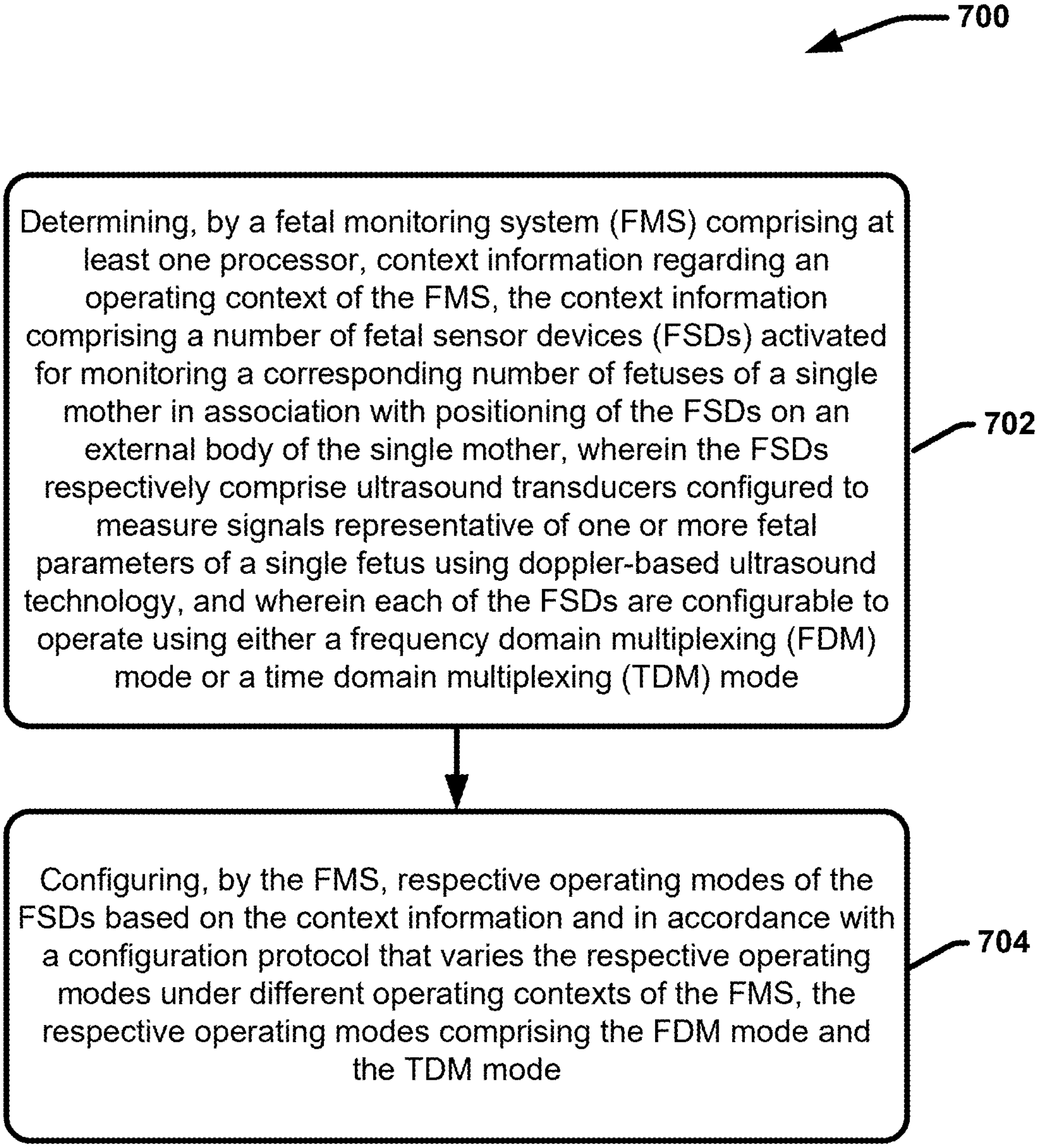
FIG. 7 illustrates a block diagram of an example, non-limiting computer implemented method of a FMS using a configuration protocol that varies respective operating modes of respective ones of the FSDs under different operating contexts, in accordance with one or more embodiments of the disclosed subject matter.

FIG. 7 illustrates a block diagram of an example, non-limiting computer implemented method 700 of a FMS (e.g., FMS 100) using a configuration protocol that varies respective operating modes of respective ones of the FSDs under different operating contexts, in accordance with one or more embodiments of the disclosed subject matter.

Method 700 comprises, at 702 determining (e.g., via master context component 502 and/or local context component 602), by a FMS comprising at least one processor (e.g., FMS 100), one or more FSDs (e.g., one or more FSDs 104 and/or one or more FSDs 600) context information regarding an operating context of the FMS, the context information comprising a number of FSDs (e.g., FSDs 104/600) activated for monitoring a corresponding number of fetuses of a single mother in association with positioning of the FSD on an external body of the single mother, wherein the FSDs respectively comprise ultrasound transducers (e.g., ultrasound transducers 618) configured to measure signals representative of one or more fetal parameters of a single fetus using doppler-based ultrasound technology, and wherein each of the FSDs are configurable to operate using either a frequency domain multiplexing (FDM) mode or a time domain multiplexing (TDM) mode. At 704, method 700 comprises configuring, by the FMS (e.g., using master configuration component 504, communication component 522, communication component 620 and/or local configuration component 604), respective operating modes of the FSDs based on the context information and in accordance with a configuration protocol that varies the respective operating modes under different operating contexts of the FMS, the respective operating modes comprising the FDM mode and the TDM mode.

Figure 8:
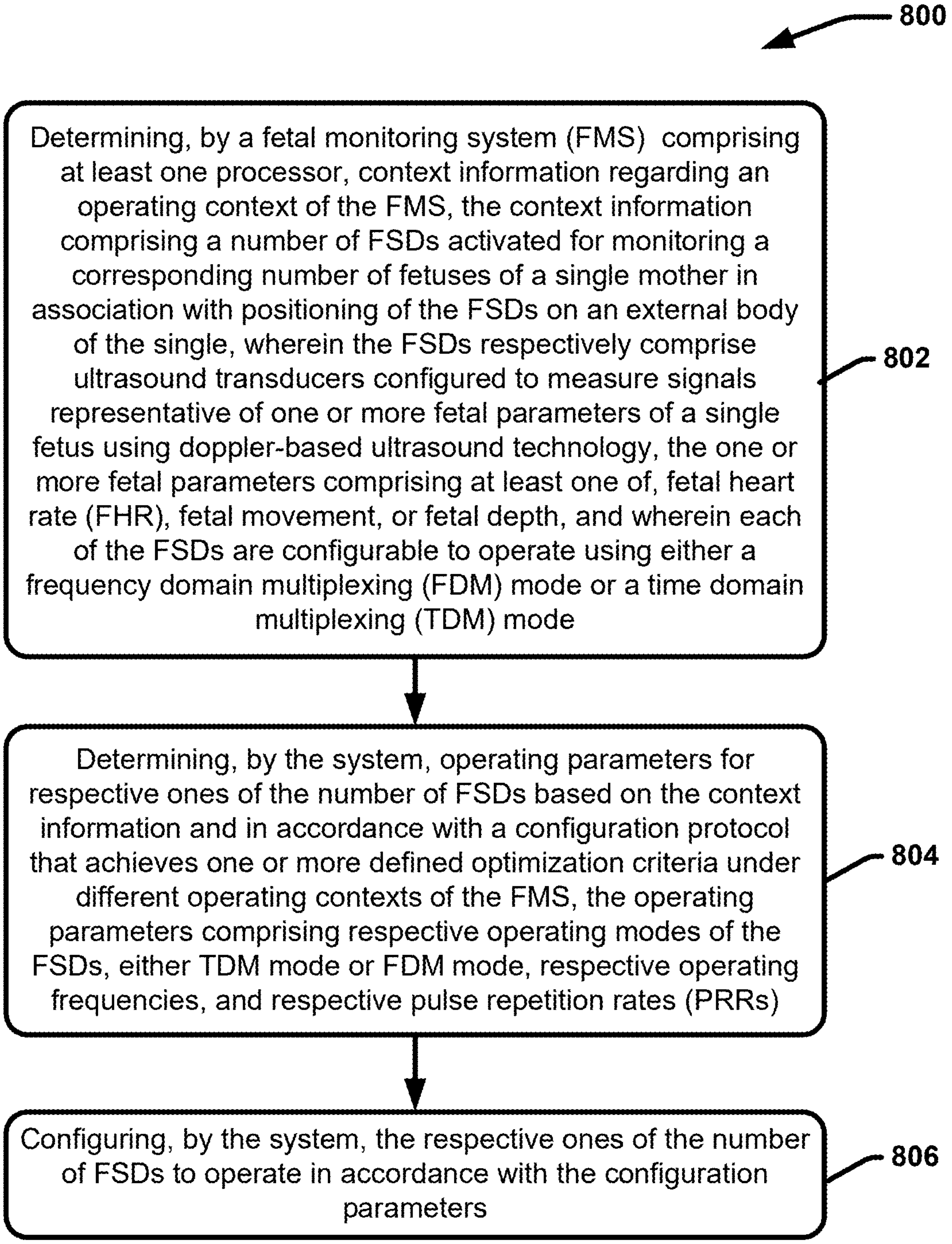
FIG. 8 illustrates a block diagram of another example, non-limiting computer implemented method of a FMS using a configuration protocol that varies respective operating modes of respective ones of the FSDs under different operating contexts, in accordance with one or more embodiments of the disclosed subject matter.

FIG. 8 illustrates a block diagram of another example non-limiting computer implemented method 800 of a FMS (e.g., FMS 100) using a configuration protocol that varies respective operating modes of respective ones of the FSDs under different operating contexts, in accordance with one or more embodiments of the disclosed subject matter. At 802, method 800 comprises determining (e.g., via master context component 502 and/or local context component 602), by a FMS comprising at least one processor (e.g., FMS 100), context information regarding an operating context of the FMS, the context information comprising a number of FSDs activated for monitoring a corresponding number of fetuses of a single mother in association with positioning of the FSDs on an external body of the single, wherein the FSDs respectively comprise ultrasound transducers configured to measure signals representative of one or more fetal parameters of a single fetus using doppler-based ultrasound technology, the one or more fetal parameters comprising at least one of, fetal heart rate (FHR), fetal movement, or fetal depth, and wherein each of the FSDs are configurable to operate using either a frequency domain multiplexing (FDM) mode or a time domain multiplexing (TDM) mode. The context information can also include the relative depths of the fetal heart or hearts within the womb to which the respective FSDs are targeted to monitor. At 804, method 800 further comprises determining, by the system (e.g., via master configuration component 504 and/or local configuration component 604), operating parameters for respective ones of the number of FSDs based on the context information and in accordance with a configuration protocol that achieves one or more defined optimization criteria under different operating contexts of the FMS, the operating parameters comprising respective operating modes of the FSDs, either TDM mode or FDM mode, respective operating frequencies, and respective PRRs. At 806, method 800 comprises configuring, by the FMS system, the respective ones of the number of FSDs to operate in accordance with the operating parameters (e.g., using master configuration component 504, communication component 522, communication component 620 and/or local configuration component 604).

Figure 9:
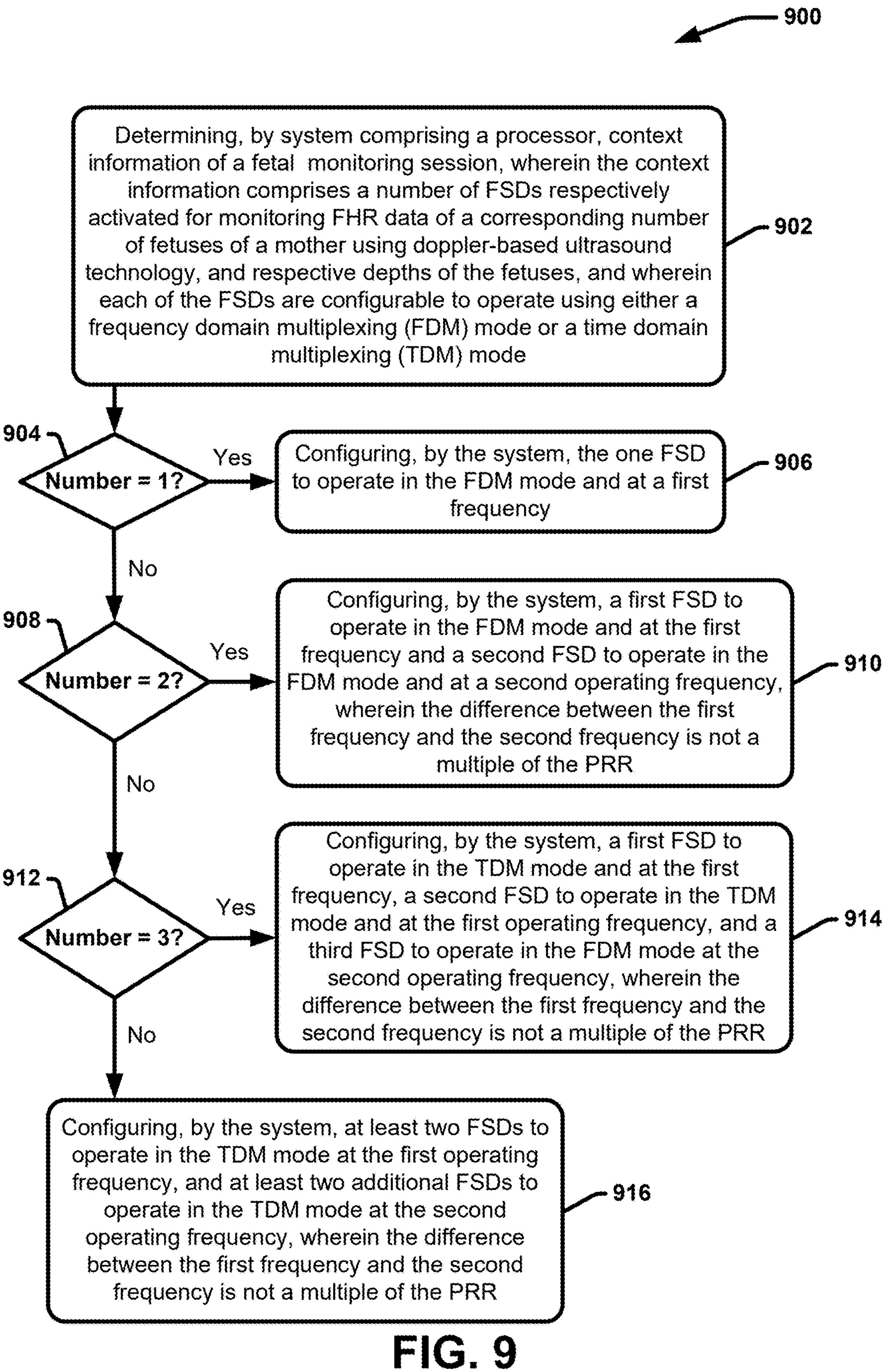
FIG. 9 illustrates a block diagram of another example, non-limiting computer implemented method of a FMS using a configuration protocol that varies respective operating modes of respective ones of the FSDs under different operating contexts, in accordance with one or more embodiments of the disclosed subject matter.

FIG. 9 illustrates a block diagram of another example non-limiting computer implemented method 900 of a FMS (e.g., FMS 100) using a configuration protocol that varies respective operating modes of respective ones of the FSDs under different operating contexts, in accordance with one or more embodiments of the disclosed subject matter. At 902, method 900 comprises determining, by system comprising a processor (e.g., FMS 100), context information of a fetal monitoring session, wherein the context information comprises a number of FSDs respectively activated for monitoring FHR data of a corresponding number of fetuses of a mother using doppler-based ultrasound technology, and respective depths of the fetuses, and wherein each of the FSDs are configurable to operate using either a frequency domain multiplexing (FDM) mode or a time domain multiplexing (TDM) mode (e.g., via master context component 502 and/or local context component 602). At 904, if the number of the FSDs is one, then method 900 continues to 906, wherein the system configures the one FSD to operate in FDM mode and at a first frequency (e.g., corresponding to the single configuration 401). In some implementations, the system can also configure the one transducer to operate a low PRR (e.g., about 3.0 kHz or less). In other implementations, the system can direct the one FSD to dynamically increase or decrease the PRR based on the detected depth of the fetus such that the resulting depth coverage corresponds to the depth of the fetus.

If at 908 the system determines the number of FSDs is two, then process 900 continues to 910 wherein the system configures a first FSD to operate in FDM mode and at the first frequency and a second FSD to operate in FDM mode at a second frequency, wherein the difference between the first and second frequency is not a multiple of the PRR (e.g., corresponding to the twin configuration 402). With these embodiments, the PRR can be set to 2.0 kHz or higher.

If at 912 the system determines the number of FSDs is three, then process 900 continues to 914 wherein the system configures a first FSD to operate in the TDM mode and at the first frequency, a second FSD to operate in the TDM mode and at the first operating frequency, and a third FSD to operate in the FDM mode at a second operating frequency, wherein the difference between the first and second frequency is not a multiple of the PRR (e.g., corresponding to the triplet configuration 403). With these embodiments, the PRR can be set to 2.0 kHz or higher.

If at 912, the system determines the number of FSD is greater than three (e.g., four or more), than process 900 continues to 916, wherein the system configures at least two FSDs to operate in the TDM mode at the first operating frequency, and at least two additional FSDs to operate in the TDM mode at the second operating frequency, wherein the difference between the first and second frequency is not a multiple of the PRR (e.g., corresponding to the quadruplet configuration 404).

In various implementations, during clinical practice in which the number of fetuses to be monitored simultaneously is greater than one (e.g., two, three, four, etc.), each FSD may be activated and applied to the mother individually and sequentially. For example, as applied to the triplet monitoring scenario, the FMS 100 may first activate and configure a single FSD (e.g., in accordance with the single configuration 401) in association with placement of the FSD on the mother's abdomen to detect a first corresponding fetal heart. Once detected, the system may then activate and configure (e.g., in accordance with the twin configuration 402) a second FSD in association with placement of the second FSD on the mother's abdomen to detect a second corresponding fetal heart. In association with configuring the second FSD, the system may reconfigure the operating parameters of the first FSD such that the combined operating parameters provide optimal depth coverage while minimizing or preventing crosstalk. Once the second fetal heart has been detected, the FMS may then activate and configure (e.g., in accordance with the triplet configuration 403) a third FSD in association with placement of the third FSD on the mother's abdomen to detect a third corresponding fetal heart. In association with configuring the third FSD, the FMS 100 may reconfigure the operating parameters of the first FSD and the second FSD such that the combined operating parameters of all three transducers provide optimal depth coverage while minimizing or preventing crosstalk. For example, in accordance with the triplet configuration 403, the FMS may dynamically reconfigure the first FSD and the second FSD to operate in TDM mode at a first frequency while at the same time configuring the third transducer to operate in FDM mode at a second frequency. With this configuration, the PRR can be set to 2.0 kHz or higher. In another example in which all three fetal hearts are positioned within a depth range enabled by a PRR of 3.0 kHz or higher, the FMS can configure/reconfigure all three FSD to operate in FDM mode at three different frequencies and at PRR of 3.0 kHz or higher. The same principle can be extended to addition of more FSDs (e.g., four, five, etc.) wherein as each additional FSD is activated, the FMS can configure/reconfigure the operating parameters all transducer devices accordingly, which can involve changing the operating mode, PRR and/or frequency settings of one or more previously configured FSDs.

Figure 10:
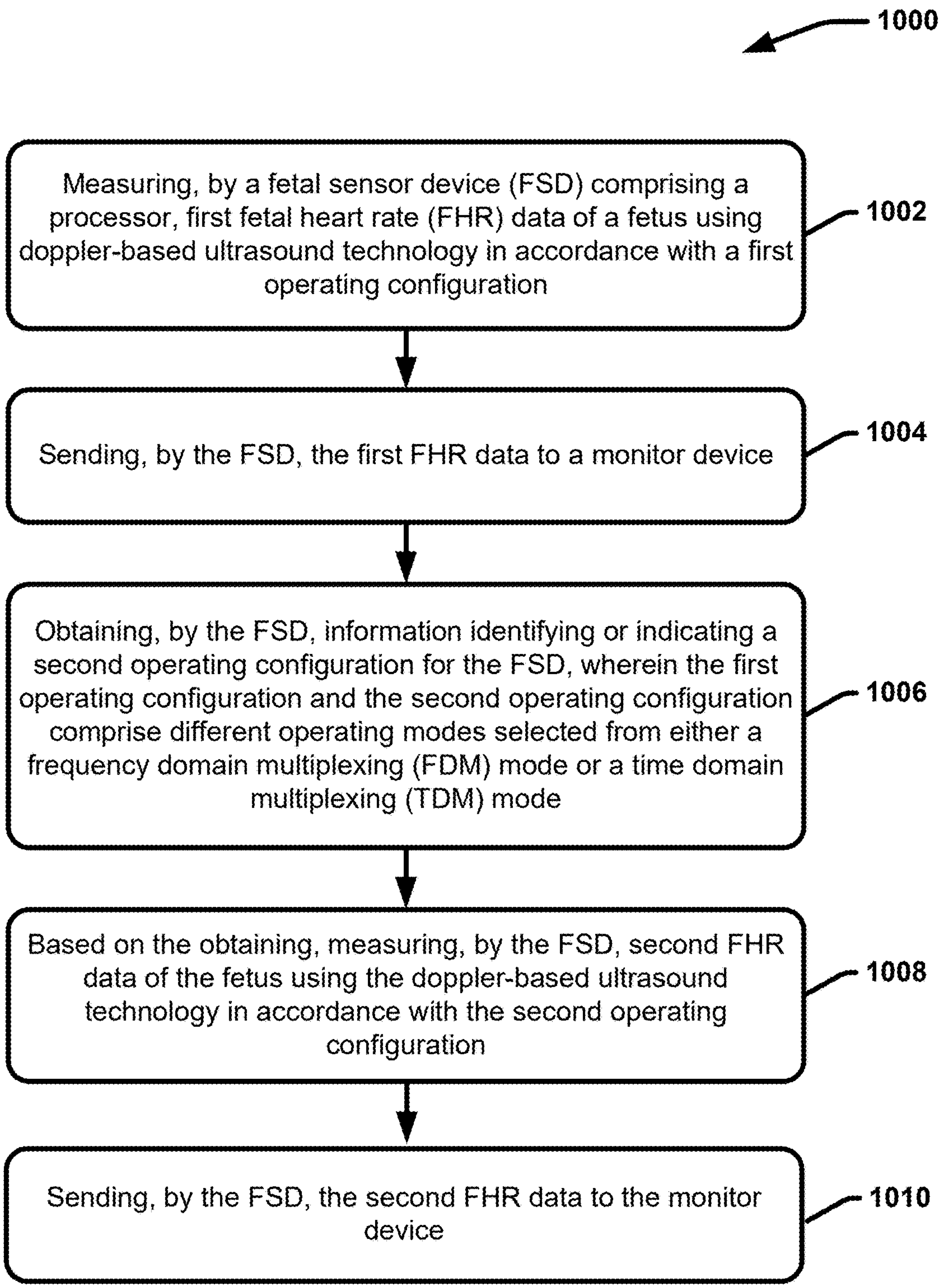
FIG. 10 illustrates a block diagram of another example, non-limiting computer implemented method of a FMS using a configuration protocol that varies respective operating modes of respective ones of the FSDs under different operating contexts, in accordance with one or more embodiments of the disclosed subject matter.

FIG. 10 another example non-limiting computer implemented method 1000 of a FMS (e.g., FMS 100) using a configuration protocol that varies respective operating modes of respective ones of the FSDs under different operating contexts, in accordance with one or more embodiments of the disclosed subject matter. Method 1000 provides an example method performed from the perspective of an FSD 104 of the FMS 100. Method 1000 comprises, at 1002 measuring (e.g., via ultrasound transducer 618), by a fetal sensor device (FSD) comprising a processor (e.g., FSD 104, FSD 600, or the like), first fetal heart rate (FHR) data of a fetus using doppler-based ultrasound technology in accordance with a first operating configuration. At 1004, method 1000 comprises sending (e.g., via communication component 620), by the FSD, the first FHR data to a monitor device (e.g., monitor device 102, monitor device 500, or the like).

At 1006, method 1000 comprises obtaining, by the FSD (e.g., via local context component 602, from the monitor device 102/500, and/or from another FSD), information identifying or indicating a second operating configuration for the FSD, wherein the first operating configuration and the second operating configuration comprise different modes selected from either a frequency domain multiplexing (FDM) mode or a time domain multiplexing (TDM) mode. For example, the information identifying or indicating the second operating configuration may include or correspond to configuration information received from the monitor device identifying the second operating configuration and instructing the FSD to switch from the first operating configuration to the second operating configuration. In another example, the information identifying or indicating the second operating configuration may include or correspond to context information determined by the FSD (e.g., via local context component 602) and/or received from the monitor device or another activated FSD indicating the number of FSDs currently activated and/or the corresponding depths of the fetuses, (wherein the number and/or the depth varies from the previous number or value), and/or respective current operating configurations of the one or more activated FSD configurations. With these embodiments, the FSD can determine any changes to its current operating configuration (e.g., changing from the first operating configuration to the second operating configuration) based on the context information and using local configuration protocol 606 and/or one or more configuration optimization functions 610.

At 1008, based on the obtaining, method 1000 comprises measuring, by the FSD, second FHR data of the fetus using the doppler-based ultrasound technology and in accordance with the second operating configuration (e.g., in association with reconfiguring the FSD via local configuration component 604) to operate in the second operating configuration as opposed to the first operating configuration). At 1010, method 1000 further comprises sending, by the FSD, the second FHR data to the monitor device.

Example Operating Environments

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. To this end, a computer readable storage medium, a machine-readable storage medium, or the like as used herein can include a non-transitory computer readable storage medium, a non-transitory machine-readable storage medium, and the like.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 11, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 11:
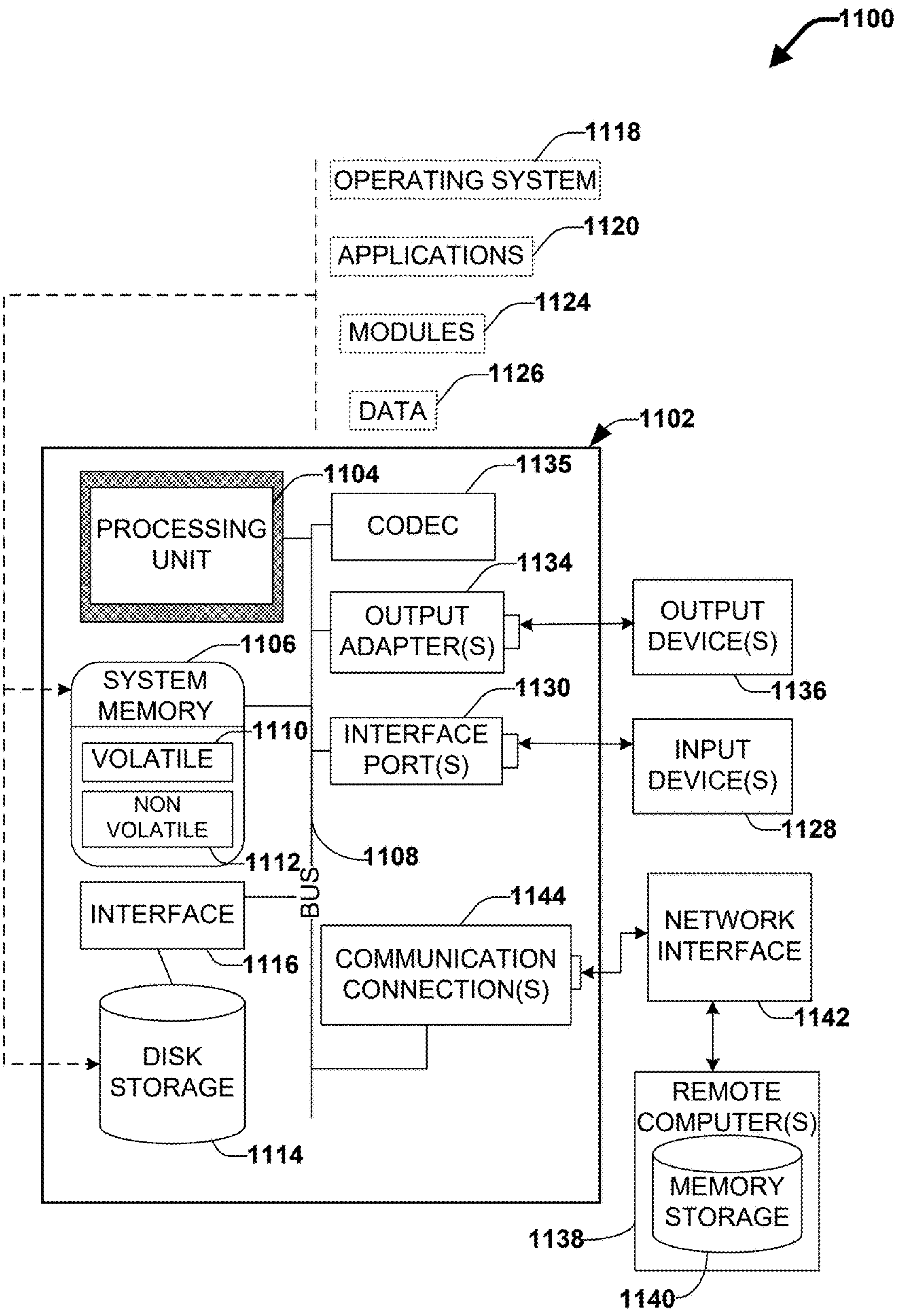
FIG. 11 illustrates a block diagram of an example, non-limiting operating environment in which one or more embodiments described herein can be facilitated.

With reference to FIG. 11, an example environment 1100 for implementing various aspects of the claimed subject matter includes a computer 1102. The computer 1102 includes a processing unit 1104, a system memory 1106, a codec 1135, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13114), and Small Computer Systems Interface (SCSI).

The system memory 1106 includes volatile memory 1110 and non-volatile memory 1112, which can employ one or more of the disclosed memory architectures, in various embodiments. The basic input/output system (BIOS), containing the basic routines to transfer information between elements within the computer 1102, such as during start-up, is stored in non-volatile memory 1112. In addition, according to present innovations, codec 1135 can include at least one of an encoder or decoder, wherein the at least one of an encoder or decoder can consist of hardware, software, or a combination of hardware and software. Although, codec 1135 is depicted as a separate component, codec 1135 can be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1112 can employ one or more of the disclosed memory devices, in at least some embodiments. Moreover, non-volatile memory 1112 can be computer memory (e.g., physically integrated with computer 1102 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1110 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1102 can also include removable/non-removable, volatile/non-volatile computer storage medium. FIG. 11 illustrates, for example, disk storage 1114. Disk storage 1114 includes, but is not limited to, devices like a magnetic disk drive, solid state disk (SSD), flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1114 to the system bus 1108, a removable or non-removable interface is typically used, such as interface 1116. It is appreciated that disk storage 1114 can store information related to a user. Such information might be stored at or provided to a server or to an application running on a user device. In one embodiment, the user can be notified (e.g., by way of output device(s) 1136) of the types of information that are stored to disk storage 1114 or transmitted to the server or application. The user can be provided the opportunity to opt-in or opt-out of having such information collected or shared with the server or application (e.g., by way of input from input device(s) 1128).

It is to be appreciated that FIG. 11 describes software that acts as an intermediary between users and the basic computer resources described in the suitable operating environment 1100. Such software includes an operating system 1110. Operating system 1110, which can be stored on disk storage 1114, acts to control and allocate resources of the computer 1102. Applications 1120 take advantage of the management of resources by operating system 1110 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems.

A user enters commands or information into the computer 1102 through input device(s) 1128. Input devices 1128 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port can be used to provide input to computer 1102 and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, and wired and wireless Ethernet cards, hubs, and routers.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A fetal monitoring system, comprising:

a plurality of fetal sensor devices, wherein each of the fetal sensor devices comprises an ultrasound transducer configured to measure signals representative of one or more fetal parameters of a single fetus using doppler-based ultrasound technology, the one or more fetal parameters comprising at least one of fetal heart rate (FHR), fetal movement, or fetal depth, and wherein each fetal sensor devices is configurable to operate in different operating modes, wherein the different operating modes comprise a frequency domain multiplexing (FDM) mode and a time domain multiplexing (TDM) mode; and at least one memory that stores computer-executable components; and at least one processor that executes the computer-executable components stored in the at least one memory, wherein the computer-executable components are configured to:

determine context information regarding an operating context of the fetal monitoring system, the context information comprising:

a number of the fetal sensor devices activated for monitoring a corresponding number of fetuses within a womb of a single mother in association with positioning of the fetal sensor devices on an external body of the single mother, and respective anatomical positions of the fetuses within the womb relative to respective external positions of the fetal sensor devices as positioned on the external body of the single mother; and configure respective operating modes of the fetal sensor devices based on the context information and in accordance with a configuration protocol that varies the respective operating modes between the different operating modes under different operating contexts of the fetal monitoring system, wherein the configuration protocol further achieves one or more defined optimization criteria under the different operating contexts, the one or more defined optimization criteria selected from a group consisting of: minimizing power consumption by the fetal sensor devices, minimizing crosstalk between the fetal sensor devices, and achieving a requisite depth coverage.

2. The fetal monitoring system of claim 1, wherein the configuration protocol comprises a hybrid configuration, and wherein based on the number of the fetal sensor devices being greater than one, the computer-executable components configure at least a first one of the fetal sensor devices to operate in the FDM mode and at least a second one of the fetal sensor devices to operate in the TDM mode, thereby enabling operating corresponding ultrasound transducers of the fetal sensor devices at lower pulse repetition rate relative to a pulse repetition rate restricted by a configuration in which the fetal sensor devices operate using a same operating mode, the same operating mode being either the FDM mode or the TDM mode.

3. The fetal monitoring system of claim 1, wherein the configuration protocol comprises switching configuring the fetal sensor devices between the FDM mode and the TDM mode based on the different operating contexts, wherein the different operating contexts correspond to different numbers of the fetal sensor devices activated for the monitoring of the corresponding number of fetuses of the single mother.

4. The fetal monitoring system of claim 3, wherein the different operating contexts account for different ones of the respective anatomical positions, and wherein the computer-executable components reconfigure one or more operating parameters of at least one of the fetal sensors devices based on a change to the operating context as determined by the computer-executable components, the one or more operating parameters comprising a current operating mode, a pulse repetition rate, and an operating frequency.

5. The fetal monitoring system of claim 1, wherein the computer-executable components further configure an operating frequency and a pulse repetition rate of the fetal sensor devices based on the context information, wherein the configuration protocol varies the operating frequency and the pulse repetition rate of the fetal sensor devices under the different operating contexts, and wherein the different operating contexts account for different ones of the respective anatomical positions.

6. The fetal monitoring system of claim 1, wherein based on the number of the fetal sensor devices being one or two fetal sensor devices, the computer-executable components configure the one or two fetal sensor devices to operate in the FDM mode.

7. The fetal monitoring system of claim 1, wherein based on the number of the fetal sensor devices being three fetal sensor devices, the computer-executable components configure two of the fetal sensors devices to operate in the TDM mode and a third fetal sensor device to operate in the FDM mode.

8. The fetal monitoring system of claim 7, wherein the computer-executable components configure the two of the fetal sensor devices operate in the TDM mode and the third fetal sensor device to operate in the FDM mode based on respective distances between the two of the fetal sensor devices, as placed on the external body of the single mother, being smaller than a distance between the third fetal sensor device, as placed on the external body of the single mother, and a corresponding heart of a third fetus.

9. The fetal monitoring system of claim 1, wherein based on the number of the fetal sensor devices being four or greater fetal sensor devices, the computer-executable components configure the four or greater fetal sensor devices to operate in the TDM mode and at two or more different operating frequencies.

10. The fetal monitoring system of claim 1, further comprising:

a monitor device, wherein the monitor device and the fetal sensor devices are communicatively coupled via one or more wired or wireless communication technologies, wherein the monitor device comprises the at least one memory and the at least one processor, and wherein the computer-executable components configure the fetal sensor devices via respective configuration command signals communicated by the monitor device to the fetal sensor devices.

11. The fetal monitoring system of claim 1, wherein each of the fetal sensor devices comprises the at least one memory that stores the computer-executable components and the at least one processor that executes the computer-executable components.

12. A method, comprising:

determining, by a fetal monitoring system comprising at least one processor, context information regarding an operating context of the fetal monitoring system, wherein the context information comprises a number of fetal sensor devices activated for monitoring a corresponding number of fetuses within a womb of a single mother in association with positioning of the fetal sensor devices on an external body of the single mother, and respective anatomical positions of the fetuses within the womb relative to respective external positions of the fetal sensor devices as positioned on the external body of the single mother, wherein each of the fetal sensor devices comprises an ultrasound transducer configured to measure signals representative of one or more fetal parameters of a single fetus using doppler-based ultrasound technology, the one or more fetal parameters comprising at least one of, fetal heart rate (FHR), fetal movement, or fetal depth, and wherein each of the fetal sensor devices is configurable to operate in different operating modes, the different operating modes comprising a frequency domain multiplexing (FDM) mode and a time domain multiplexing (TDM) mode; and configuring, by the fetal monitoring system, respective operating modes of the fetal sensor devices based on the context information and in accordance with a configuration protocol that varies the respective operating modes between the different operating modes under different operating contexts of the fetal monitoring system, wherein the configuration protocol further achieves one or more defined optimization criteria under the different operating contexts, the one or more defined optimization criteria selected from a group consisting of: minimizing power consumption by the fetal sensor devices, minimizing crosstalk between the fetal sensor devices, and achieving a requisite depth coverage.

13. The method of claim 12, wherein the configuration protocol comprises a hybrid configuration, and wherein based on the number of the fetal sensor devices being greater than two, the configurating comprises configurating at least a first one of the fetal sensor devices to operate in the FDM mode and at least a second one of the fetal sensor devices to operate in the TDM mode, thereby enabling operating corresponding ultrasound transducers of the fetal sensor devices at lower pulse repetition rate relative to a pulse repetition rate restricted by a configuration in which the fetal sensor devices operate using a same operating mode, the same operating mode either the FDM mode or the TDM mode.

14. The method of claim 12, wherein the configuration protocol comprises switching configuring the fetal sensor devices between the FDM mode and the TDM mode based on the different operating contexts, and wherein the different operating contexts correspond to different numbers of the fetal sensor devices activated for the monitoring of the corresponding number of fetuses of the single mother.

15. The method of claim 14, wherein the different operating contexts account for different ones of the respective anatomical positions.

16. The method of claim 15, further comprising:

reconfiguring, by the fetal monitoring system, one or more operating parameters of at least one of the fetal sensors devices based on a change to the operating context, the one or more operating parameters comprising a current operating mode, a pulse repetition rate, and an operating frequency.

17. A non-transitory machine-readable storage medium, comprising executable instructions that, when executed by a processor of a fetal monitoring system, facilitate performance of operations, comprising:

determining context information regarding an operating context of the fetal monitoring system, wherein the context information comprises a number of fetal sensor devices activated for monitoring a corresponding number of fetuses within a womb of a single mother in association with positioning of the fetal sensor devices on an external body of the single mother, and respective anatomical positions of the fetuses within the womb relative to respective external positions of the fetal sensor devices as positioned on the external body of the single mother, wherein each the fetal sensor devices comprises an ultrasound transducer configured to measure signals representative of one or more fetal parameters of a single fetus using doppler-based ultrasound technology, the one or more fetal parameters comprising at least one of, fetal heart rate (FHR), fetal movement, or fetal depth, and wherein each of the fetal sensor devices is configurable to operate in different operating modes, the different operating modes comprising a frequency domain multiplexing (FDM) mode and a time domain multiplexing (TDM) mode; and configuring respective operating modes of the fetal sensor devices based on the context information and in accordance with a configuration protocol that varies the respective operating modes between the different operating modes under different operating contexts of the fetal monitoring system, wherein the configuration protocol further achieves one or more defined optimization criteria under the different operating contexts, the one or more defined optimization criteria selected from a group consisting of: minimizing power consumption by the fetal sensor devices, minimizing crosstalk between the fetal sensor devices, and achieving a requisite depth coverage.

18. The non-transitory machine-readable storage medium of claim 17, wherein the configuration protocol comprises a hybrid configuration, and wherein based on the number of the fetal sensor devices being greater than two, the configurating comprises configurating at least a first one of the fetal sensor devices to operate in the FDM mode and at least a second one of the fetal sensor devices to operate in the TDM mode, thereby enabling operating corresponding ultrasound transducers of the fetal sensor devices at lower pulse repetition rate relative to a pulse repetition rate restricted by a configuration in which the fetal sensor devices operate using a same operating mode, the same operating mode either the FDM mode or the TDM mode.

19. The non-transitory machine-readable storage medium 17, wherein the configuration protocol comprises switching configuring the fetal sensor devices between the FDM mode and the TDM mode based on the different operating contexts, and wherein the different operating contexts correspond to different numbers of the fetal sensor devices activated for the monitoring of the corresponding number of fetuses of the single mother.

20. The non-transitory machine-readable storage medium of claim 19, wherein the different operating contexts account for different ones of the respective anatomical positions, and wherein the operations further comprise:

reconfiguring one or more operating parameters of at least one of the fetal sensor devices based on a change to the operating context, the one or more operating parameters comprising a current operating mode, a pulse repetition rate, and an operating frequency.

* * * * *